(12) United States Patent
Jiang et al.

(10) Patent No.: US 9,150,530 B2
(45) Date of Patent: Oct. 6, 2015

(54) ESTERS OF 4, 9-DIHYDROXY-NAPHTHO [2, 3-B] FURANS FOR DISEASE THERAPIES

(75) Inventors: Zhiwei Jiang, Zhejiang (CN); Aijin Wang, Zhejiang (CN); Hongwei Hu, Zhejiang (CN); Jiali Xu, Zhejiang (CN); Yuesong Hu, Zhejiang (CN); Xian Li, Zhejiang (CN); Yan Ye, Zhejiang (CN); Jie Wang, Zhejiang (CN); Qinglong Li, Zhejiang (CN)

(73) Assignee: Zhoushan Haizhongzhou Xinsheng Pharmaceuticals Co., Ltd., Zhoushan, Zhejiang (CN)

( * ) Notice: Subject to any disclaimer, the term of this patent is extended or adjusted under 35 U.S.C. 154(b) by 0 days.

(21) Appl. No.: 14/002,986

(22) PCT Filed: Mar. 4, 2011

(86) PCT No.: PCT/CN2011/000357
§ 371 (c)(1),
(2), (4) Date: Sep. 3, 2013

(87) PCT Pub. No.: WO2012/119265
PCT Pub. Date: Sep. 13, 2012

(65) Prior Publication Data
US 2013/0345176 A1 Dec. 26, 2013

(51) Int. Cl.
*A61K 31/34* (2006.01)
*C07D 307/92* (2006.01)
*A61K 31/343* (2006.01)
*A61K 31/665* (2006.01)
*A61K 45/06* (2006.01)
*C07F 9/655* (2006.01)

(52) U.S. Cl.
CPC ............ *C07D 307/92* (2013.01); *A61K 31/343* (2013.01); *A61K 31/665* (2013.01); *A61K 45/06* (2013.01); *C07F 9/65517* (2013.01)

(58) Field of Classification Search
CPC ... A61K 31/343; A61K 31/665; A61K 45/06; C07F 9/65517; C07D 307/92
USPC ........... 514/449, 461, 468; 549/429, 456, 458
See application file for complete search history.

(56) References Cited

U.S. PATENT DOCUMENTS 8,871,802 B2 * 10/2014 Jiang et al. ..................... 514/468
2013/0150437 A1 * 6/2013 Jiang et al. ..................... 514/468

FOREIGN PATENT DOCUMENTS

| CN | 101854930 A | 10/2010 |
| CN | 101854937 A | 10/2010 |
| JP | 2010-539095 A | 12/2010 |
| JP | 2010-539097 A | 12/2010 |
| WO | WO2009/036059 | 3/2009 |
| WO | WO2009/036099 | 3/2009 |

OTHER PUBLICATIONS

International Search Report for PCT/CN2011/000357, 6 pages (Dec. 8, 2011).
De Oliveira, A. B. et al., Lignans and naphthoquinones from *Tabebuia incana*, Phytochemistry, 34(5): 1409-12 (1993).
Takano, A. et al., Tumor-specific cytotoxicity and type of cell death induced by naphtho[2,3-b]furan-4,9-diones and related compounds in human tumor cell lines: relationship to electronic structure, Anticancer Research, 29(1):455-64 (2009).
Supplementary European Search Report for EP 11 86 0457.8 dated Jul. 2, 2014.
Grinev et al., Synthesis of derivatives of naphtho[2,3-b] furan-4, 9-dione, Chemistry of Heterocyclic Compounds, 6(7):803-6 (1970).
Kucklander, U., Mechamism of the Nenitzescu Reaction, V1. Synthesis of Naphthofuran Derivatives, Justus Liebigs Annalen der Chemie, 1978(1):140-9 (1978). English Abstract Only.
Otsuki, T., Photo-induced reaction of 2-alkoxy-3-bromo-1, 4-naphthoquinones with acetylenes: Formation of 2-aryl-substituted naptho[2,3-b]furan-4, 9-diones, Bulletin of the Chemical Society of Japan, 49(12):3713-4 (1976).
Pratt et al., Reactions of Napthoquinones with Malonic Ester and its Analogs. IV. A Synthesis of 2,3-disubstituted-4,5-phthaloylfurans, Synthesis of 2,3-Disubstituted-4,5-Phthaloylfurans, Contribution from the Department of Chemistry, University of Maryland, 5489-97 (1957),<http://pubs.acs.org/doi/pdf/10.1021/ja01577a043> retrieved on Jun. 17, 2014.
Chatterjea, J.N. et al., Synthesis of furano compounds. XXXII., Synthesis of some β-brazanquinones derived from natural sources, Journal of the Indian Chemical Society, 47(6): 567-575 (1970).
Hewgill, F.R. and Mullings, L.R., ESR studies of some polycyclic semiquinones and derived radicals, Australian Journal of Chemistry, 28(2): 355-367 (1975).
Rao, M.M. et al., Plant anticancer agents. XII., Isolation and structure elucidation of new cytotoxic quinones from *Tabebuia cassinoides*, Journal of Natural Products, 45(5): 600-604 (1982).
Sugimoto, I. and Takahashi, Y., Solvates, non-crystalline chemicals pharmaceutical production, Journal of Society of Powder Technology, 22(2): 85-97 (1985).

* cited by examiner

*Primary Examiner* — My-Chau T Tran
(74) *Attorney, Agent, or Firm* — Choate, Hall & Stewart, LLP; Fangli Chen; John P. Rearick

(57) ABSTRACT

The present invention discloses esters of 4,9-dihydroxy-naphtho[2,3-b]furans and methods of making and using the same. The present invention also discloses conversion of the esters into therapeutically active 4,9-dihydroxy-naphtho[2,3-b]furans in vivo. The present invention furthermore discloses pharmaceutical compositions comprising the esters of 4,9-dihydroxy-naphtho[2,3-b]furans for the treatment of various indications including proliferative diseases.

31 Claims, 15 Drawing Sheets

(A) Compound I:

(B) Human plasma incubated Compound I:

(C) Compound IV:

(D) Human plasma incubated Compound IV:

(E) 2-acetyl-4,9-bis(acetoxy)-naphtho[2,3-b]furan:

(F) Human plasma incubated 2-acetyl-4,9-bis(acetoxy)-naphtho[2,3-b]furan:

(A)

(B)

(A) Relative NQ01 activities in different cancer cell lines measured by using the method as reported (Pink J J, et al. J. of Biol. Chem., 2000, 275: 5416-5424)

(B) Dicumarol effect on the biological activity of compound XIII in DLD1 cells or in Panc-1 cells.

(C) Dicumarol effect on the biological activity of 2-acetyl-4,9-bis(acetoxy)-naphtho[2,3-b]furan in DLD1 cells or in Panc-1 cells.

Control $H_2O_2$

Compound V

Compound VII

Compound XI　　　　　　　　Compound XIII (D):

(E):

(F):

ESTERS OF 4, 9-DIHYDROXY-NAPHTHO [2, 3-B] FURANS FOR DISEASE THERAPIES

BACKGROUND OF THE INVENTION

One type of the naturally occurring compounds with broad therapeutic applications is quinone. Quinone compounds widely exist in microorganisms, plants and animals (Thomson R H *Naturally Occurring Quinones IV: Recent Advances*. Published by Springer, 1996). Quinone compounds are redox capable and exist in vivo in one or several chemical species. Coenzyme Q10 is one of a few quinone compounds with fully identified chemical species profile in vivo (Bhagavan H N, et al. *Mitochondrion,* 2007, 7S: S78-88). The circulating coenzyme Q10 in human is almost entirely in the form of hydroquinone and the conversion to hydroquinone of the orally administered ubiquinone (oxidized form of coenzyme Q10) occurs in the enterocytes prior to its lymphatic transport into circulation (Craft N E, et al. *FASEB J.* 2005, 19, A449; Bhagavan H N, et al. *Int. J. Pharmaceut.* 2007, 333: 112-117; Mohr D, et al. *Redox Rep.* 1999, 4: 79-87).

Approved anticancer quinone compounds include daunorubicin, doxorubicin, epirubicin, idarubicin, valrubicin, and mitomycin. Their anticancer activity is mainly attributed to their ability to inhibit DNA replication in cancer cells by directly damaging DNA or interacting with proteins involved in DNA replication. Naphthofuran quinones have also a variety of biological activities. Some of them have been shown to have anticancer and other activities. For example, several natural occurring naphtho[2,3-b]furan-4,9-diones with interesting biological activities have been isolated from plants (Rao M M, et al. *J. Natural Products,* 1982, 45: 600-604; Tisler M, "Heterocyclic Quinones in Advances in Heterocyclic Chemistry" Vol. 45, ed. Katritzky A R, Academic Press, London, 1989, 56-63), and their analogs have further been found to have cytotoxic activity (Ogawa M, et al. *Bioscience, Biotechnology, and Biochemistry,* 2006, 70: 1009-1012; US20060142271; WO2009036059; WO2009036099; WO2009036101).

As cancer is a leading cause of death worldwide, accounting for 13% of all deaths according to 2004 World Health Organization statistics, there remains a need for novel compounds as active pharmaceutical ingredient useful for more effective treatment of cancer.

SUMMARY

The present invention provides novel compounds as active pharmaceutical ingredients for more effective treatment of cancer and other diseases, disorders and conditions.

Among other things, the present invention provides a compound of formula I:

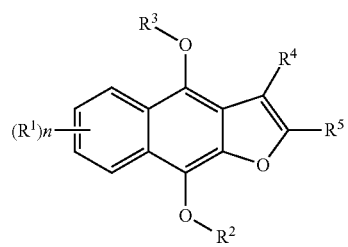

I or a pharmaceutically acceptable salt thereof;

wherein each of $R^1$, $R^2$, $R^3$, $R^4$, $R^5$ and n is as defined and described herein.

In addition, the present invention relates to conversion of the esters into therapeutically active 4,9-dihydroxy-naphtho [2,3-b]furans in vivo.

Further, the present invention relates to therapeutic activity of 4,9-dihydroxy-naphtho[2,3-b]furans mainly attributing to their ability to induce reactive oxygen species (ROS).

Furthermore, the present invention relates to pharmaceutical compositions comprising compounds described herein and use of the said compounds and compositions in the treatment of various diseases, disorders, and conditions.

Even furthermore, the present invention relates to amorphous solids of esters of 4,9-dihydroxy-naphtho[2,3-b]furans or naphtho[2,3-b]furan-4,9-diones as component of pharmaceutical composition for the treatment of various indications including proliferative diseases.

DEFINITIONS

Figure 1:
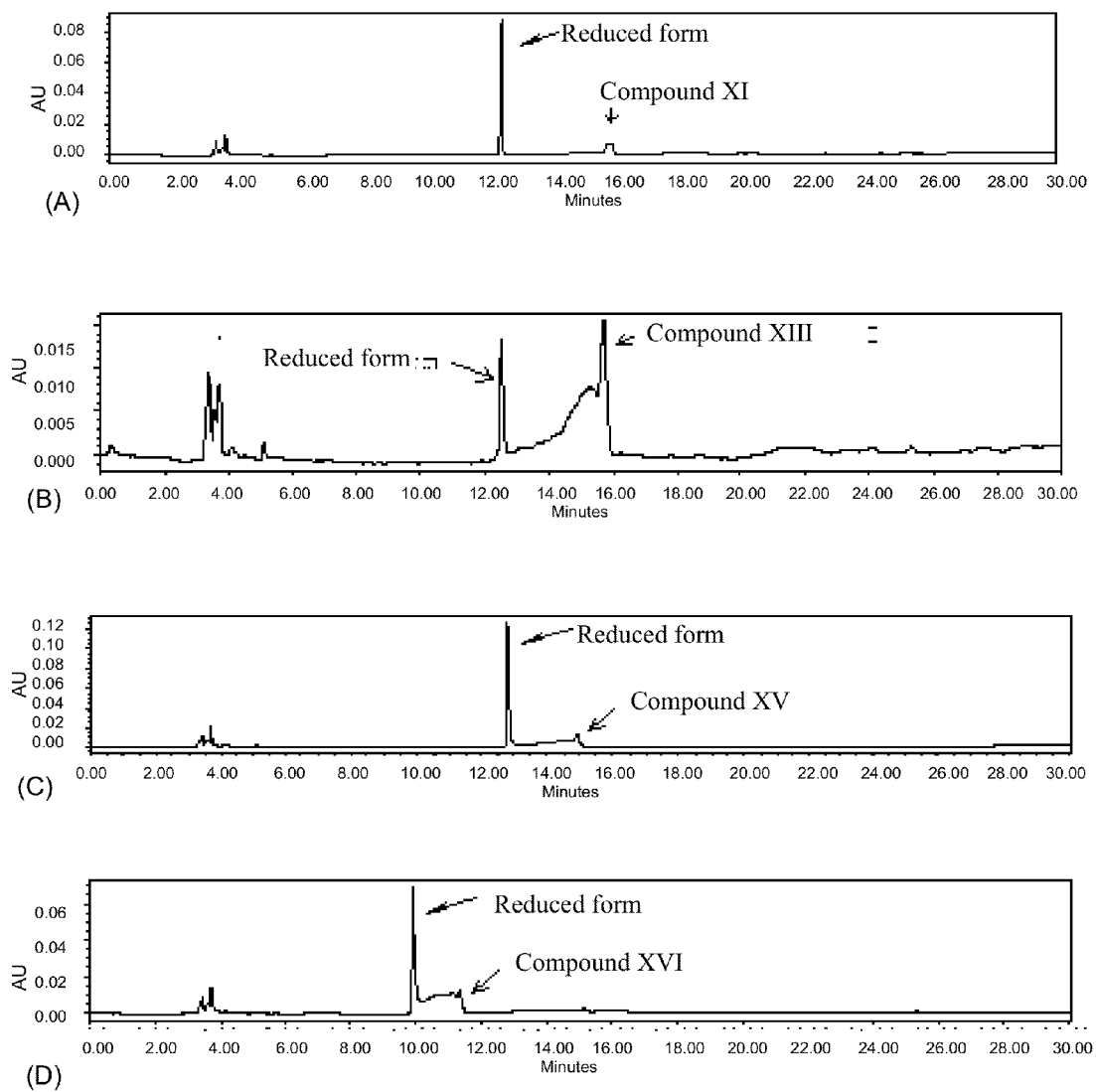
FIG. 1. HPLC chromatography of the reaction mixture of sodium hydrosulfite and various naphtho[2,3-b]furan-4,9-diones. (A) naphtho[2,3-b]furan-4,9-dione (Compound XI); (B) 2-acetyl-naphtho[2,3-b]furan-4,9-dione (Compound XIII); (C) 2-methylsulfonyl-naphtho[2,3-b]furan-4,9-dione (Compound XV); (D) 2-methylsulfinyl-naphtho[2,3-b]furan-4,9-dione (Compound XVI).

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. In certain embodiments, the term "3- to 14-membered carbocycle" and refers to a 3- to 8-membered saturated or partially unsaturated monocyclic carbocyclic ring, or a 7- to 14-membered saturated or partially unsaturated polycyclic carbocyclic ring.

The term "alkyl," as used herein, refers to saturated, straight- or branched-chain hydrocarbon derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms. In some embodiments, alkyl groups contain 1-4 carbon atoms. In certain embodiments, alkyl groups contain 1-3 carbon atoms. In some embodiments, alkyl groups contain 1-2 carbon atoms. Examples of alkyl group include, but are not limited to, methyl, ethyl, n-propyl, isopropyl, n-butyl, isobutyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms. In some embodiments, alkenyl groups contain 2-4 carbon atoms. In some embodiments, alkenyl groups contain 2-3 carbon atoms. In some embodiments, alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)). The term "unsaturated," as used herein, means that a moiety has one or more units of unsaturation.

The term "acyl," used alone or a part of a larger moiety, refers to groups formed by removing a hydroxy group from a carboxylic acid.

The term "halogen" means F, Cl, Br, or I.

The term "aryl" used alone or as part of a larger moiety as in or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. In certain embodiments, the term "6- to 14-membered aryl" refers to a phenyl or an 8- to 14-membered polycyclic aryl ring.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted. In certain embodiments, the term "5- to 14-membered heteroaryl" refers to a 5- to 6-membered heteroaryl ring having 1 to 4 heteroatoms independently selected from nitrogen, oxygen, or sulfur, or an 8- to 14-membered polycyclic heteroaryl ring having 1 to 4 heteroatoms independently selected from nitrogen, oxygen, or sulfur.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$PH which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NRO$_2$; —N(R$^\circ$)C(S)NRO$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$)$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, —SC(S)SR$^\circ$; —(CH$_2$)$_{0-4}$SC(O)R$^\circ$; —(CH$_2$)$_{04}$C(O)NRO$_2$; —C(S)NRO$_2$; —C(S)SR$^\circ$; —SC(S)SR$^\circ$, —(CH$_2$)$_{0-4}$OC(O)NRO$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NRO$_2$; —N(R$^\circ$)S(O)$_2$R$^\circ$; —N(OR$^\circ$)R$^\circ$; —C(NH)NRO$_2$; —P(O)$_2$R$^\circ$; —P(O)R$^\circ_2$; —OP(O)RO$_2$; —OP(O)(OR$^\circ$)$_2$; —SiR$^\circ_3$; —(C$_{1-4}$ straight or branched)alkylene)O—N(RO$_2$; or —(C$_{1-4}$ straight or branched)alkylene)C(O)O—N(RO$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR, =NNHC(O)R*$_2$, =NNHC(O)OR*, =NNHS(O)$_2$R*, =NR*, =NOR*, —O(C(R*$_2$))$_{2-3}$O—, or —S(C(R*$_2$))$_{2-3}$—, wherein each independent occurrence of R* is selected from hydrogen, C$_1$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\setminus$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "amorphous" is used to describe the physical form of a solid in which there is no long-range order of the position of the atoms.

As used herein and in the claims, the singular forms "a", "an", and "the" include the plural reference unless the context clearly indicates otherwise. Thus, for example, a reference to "a compound" includes a plurality of such compounds.

The terms "administer," "administering," or "administration," as used herein, refer to either directly administering a compound or composition to a patient.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "prodrug" means an agent that is converted into the parent drug in vivo. In certain embodiments, a prodrug is easier to administer than a parent drug. In certain embodiments, a prodrug has improved bioavailability by oral administration compared to the parent drug. Prodrugs may also have improved stability in pharmaceutical compositions over the parent drug. In certain embodiments, a prodrug has reduced toxicity compared to the parent drug by avoiding unnecessary exposure to unintended target tissues.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

As used herein, the "blood-brain barrier" refers to the barrier between the peripheral circulation and the brain and spinal cord which is formed by tight junctions within the brain capillary endothelial plasma membranes, creates an extremely tight barrier that restricts the transport of molecules into the brain, even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to herein as the blood-brain barrier or BBB.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

DETAILED DESCRIPTION OF CERTAIN EMBODIMENTS

The present invention provides, among other things, novel chemotherapeutics that are useful for the treatment of proliferative and other diseases, disorders, and conditions.

In certain embodiments, the present invention provides a compound of formula I:

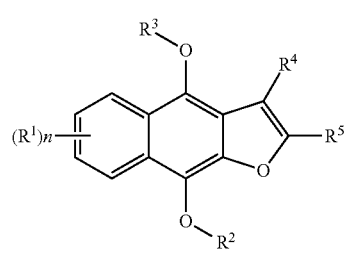

or a pharmaceutically acceptable salt thereof;
wherein:
n is 0-4;
each $R^1$ is independently halogen; —$NO_2$; —CN; —OR; —SR; —$N^+(R)_3$; —$N(R)_2$; —C(O)R; —$CO_2R$; —C(O)C(O)R; —C(O)$CH_2$C(O)R; —S(O)R; —$S(O)_2R$; —C(O)N(R)$_2$; —$SO_2N(R)_2$; —OC(O)R; —N(R)C(O)R; —N(R)N(R)$_2$; —N(R)C(=NR)N(R)$_2$; —C(=NR)N(R)$_2$; —C=NOR; —N(R)C(O)N(R)$_2$; —N(R)$SO_2$N(R)$_2$; —N(R)$SO_2$R; —OC(O)N(R)$_2$; or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl; or:
two $R^1$ groups on adjacent carbon atoms are taken together with their intervening atoms to form an optionally substituted ring selected from 3- to 14-membered carbocycle; 3- to 14-membered heterocycle; a 6- to 14-membered aryl ring; or a 5- to 14-membered heteroaryl ring;

each $R^2$ and $R^3$ is independently hydrogen, —S(=O)$_2$OR$^a$, —P(=O)OR$^a$OR$^b$, —C(=O)R$^c$; wherein each R$^a$ and R$^b$ is independently hydrogen, sodium, potassium, amine cation, or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl; or:

R$^a$ and R$^b$ are taken together with their intervening atoms to form an optionally substituted 3- to 14-membered heterocycle;

R$^c$ is hydrogen; —N(R)$_2$; —OR; —SR; or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl;

$R^4$ is independently hydrogen; halogen; —NO$_2$; —OR; —SR; —N$^+$(R)$_3$; —N(R)$_2$; —C(O)R; —CO$_2$R; —C(O)C(O)R; —C(O)CH$_2$C(O)R; —S(O)R; —S(O)$_2$R; —C(O)N(R)$_2$; —SO$_2$N(R)$_2$; —OC(O)R; —N(R)C(O)R; —N(R)N(R)$_2$; —N(R)C(=NR)N(R)$_2$; —C(=NR)N(R)$_2$; —C=NOR; —N(R)C(O)N(R)$_2$; —N(R)SO$_2$N(R)$_2$; —N(R)SO$_2$R; —OC(O)N(R)$_2$; or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl; or:

$R^4$ and $R^5$ are taken together with their intervening atoms to form an optionally substituted ring selected from 3- to 14-membered carbocycle or 3- to 14-membered heterocycle;

$R^5$ is independently halogen; —NO$_2$; —CN; —OR; —SR; —N$^+$(R)$_3$; —N(R)$_2$; —C(O)R; —CO$_2$R; —C(O)C(O)R; —C(O)CH$_2$C(O)R; —S(O)R; —S(O)$_2$R; —C(O)N(R)$_2$; —SO$_2$N(R)$_2$; —OC(O)R; —N(R)C(O)R; —N(R)N(R)$_2$; —N(R)C(=NR)N(R)$_2$; —C(=NR)N(R)$_2$; —C=NOR; —N(R)C(O)N(R)$_2$; —N(R)SO$_2$N(R)$_2$; —N(R)SO$_2$R; —OC(O)N(R)$_2$; or an optionally substituted group selected from $C_{1-12}$ aliphatic, 3- to 14-membered carbocyclyl; 3- to 14-membered heterocyclyl; 6- to 14-membered aryl; or 5- to 14-membered heteroaryl; or:

$R^4$ and $R^5$ are taken together with their intervening atoms to form an optionally substituted ring selected from 3- to 14-membered carbocycle or 3- to 14-membered heterocycle;

each R is independently hydrogen or an optionally substituted group selected from $C_{1-12}$ aliphatic; 3- to 14-membered carbocyclyl; 3- to 14-membered heterocyclyl; a 6- to 14-membered aryl; or 5- to 14-membered heteroaryl.

In some embodiments, $R^5$ is not methyl. In some embodiments, $R^5$ is not ethyl.

In some embodiments, when $R^2$ and $R^3$ are each acetyl, then $R^1$ is not acetoxy.

In some embodiments, when $R^2$ and $R^3$ are each acetyl and $R^4$ is ethoxycarbonyl, then $R^5$ is not 2-oxo-propyl.

In some embodiments, when $R^2$, $R^3$, and $R^5$ are each acetyl, then either $R^1$ or $R^4$ is not hydrogen.

In some embodiments, n is 0. In some embodiments, n is 1. In some embodiments, n is 2. In some embodiments, n is 3. In some embodiments, n is 4.

In certain embodiments, $R^1$ is halogen. In some embodiments, $R^1$ is —CN. In some embodiments, $R^1$ is —CF$_3$. In some embodiments, $R^1$ is —OH.

In some embodiments, $R^2$ is hydrogen. In some embodiments, $R^2$ is —C(=O)R$^c$, wherein R$^c$ is optionally substituted $C_{1-12}$ aliphatic. In some embodiments, $R^2$ is —P(=O)OR$^a$OR$^b$, wherein R$^a$ and R$^b$ are each independently hydrogen, sodium, potassium, or optionally substituted $C_{1-12}$ aliphatic. In some embodiments, $R^2$ is —S(=O)$_2$OR$^a$, wherein R$^a$ is hydrogen, sodium, or potassium.

In some embodiments, $R^3$ is hydrogen. In some embodiments, $R^3$ is —C(=O)R$^c$, wherein R$^c$ is optionally substituted $C_{1-12}$ aliphatic. In some embodiments, $R^3$ is —P(=O)OR$^a$OR$^b$, wherein R$^a$ and R$^b$ are each independently hydrogen, sodium, potassium, or optionally substituted $C_{1-12}$ aliphatic. In some embodiments, $R^3$ is —S(=O)$_2$OR$^a$, wherein R$^a$ is hydrogen, sodium, or potassium.

In some embodiments, $R^4$ is hydrogen. In some embodiments, $R^4$ is other than hydrogen. In some embodiments, $R^4$ is optionally substituted 6- to 14-membered aryl. In some embodiments, $R^4$ is optionally substituted phenyl. In some embodiments, $R^4$ is —N(R)$_2$, wherein R is independently an optionally substituted group selected from $C_{1-12}$ aliphatic or 6- to 14-membered aryl.

In certain embodiments, $R^5$ is —NO$_2$. In some embodiments, $R^5$ is —C(O)R, wherein R is an optionally substituted group selected from $C_{1-12}$ aliphatic or 6- to 14-membered aryl. In some embodiments, $R^5$ is —C(O)N(R)$_2$, wherein each R is independently an optionally substituted group selected from $C_{1-12}$ aliphatic or 6- to 14-membered aryl.

In certain embodiments, $R^4$ and $R^5$ are taken together with their intervening atoms to form an optionally substituted ring selected from 3- to 14-membered carbocycle or 3- to 14-membered heterocycle.

In some embodiments, $R^1$ is halogen, cyano, or CF$_3$; n is 0, 1, or 2; $R^2$ and $R^3$ are each independently hydrogen, isobutyryl, pivaloyl, acetyl, N-(tert-butoxycarbonyl)glycinyl, or N,N-dimethylglycinyl; $R^4$ is hydrogen or —N(R)$_2$; and $R^5$ is —C(O)R, wherein R is an optionally substituted group selected from $C_{1-12}$ aliphatic or 6- to 14-membered aryl. In some embodiments, $R^1$ is halogen or CF$_3$; n is 0, 1, or 2; $R^2$ and $R^3$ are each independently acetyl or N-(tert-butoxycarbonyl)glycinyl; $R^4$ is hydrogen; and $R^5$ is —C(O)R, wherein R is optionally substituted $C_{1-12}$ aliphatic.

Exemplary compounds of formula I are set forth in table 1 below.

TABLE 1 compound I

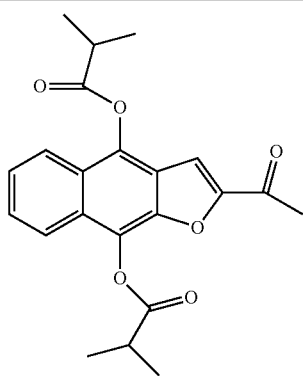 [SMILES: CC(=O)c1cc2c(OC(=O)C(C)C)c3ccccc3c(OC(=O)C(C)C)c2o1]

TABLE 1-continued
compound II
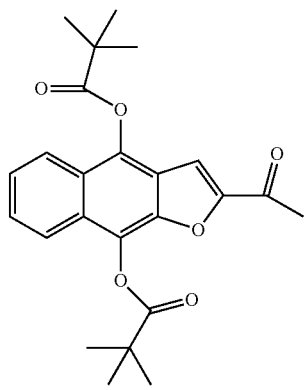 [SMILES: CC(=O)c1cc2c(OC(=O)C(C)(C)C)c3ccccc3c(OC(=O)C(C)(C)C)c2o1]
compound III
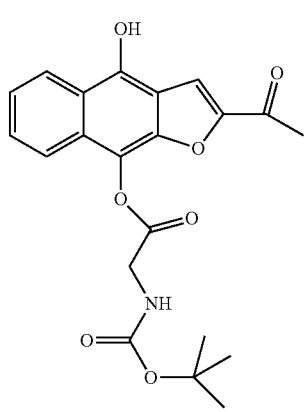 [SMILES: CC(=O)c1cc2c(O)c3ccccc3c(OC(=O)CNC(=O)OC(C)(C)C)c2o1]
compound IV
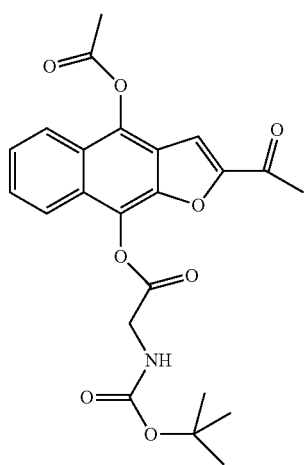 [SMILES: CC(=O)Oc1c2ccccc2c(OC(=O)CNC(=O)OC(C)(C)C)c2oc(C(C)=O)cc12]
TABLE 1-continued
compound V
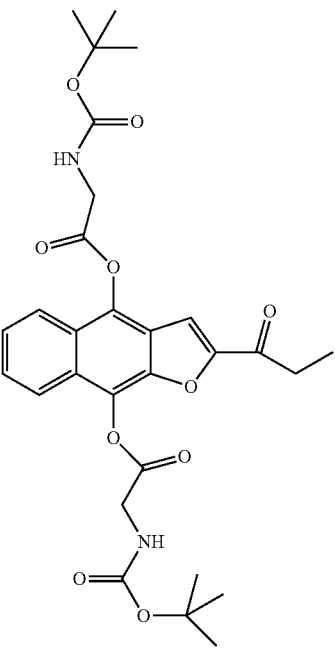 [SMILES: CCC(=O)c1cc2c(OC(=O)CNC(=O)OC(C)(C)C)c3ccccc3c(OC(=O)CNC(=O)OC(C)(C)C)c2o1]
compound VI
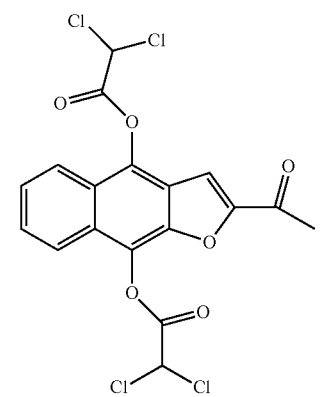 [SMILES: CC(=O)c1cc2c(OC(=O)C(Cl)Cl)c3ccccc3c(OC(=O)C(Cl)Cl)c2o1]
compound VII
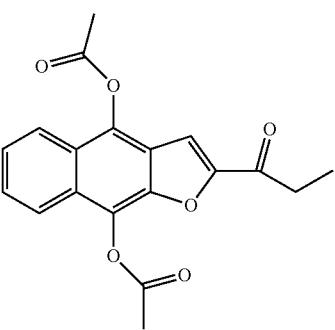 [SMILES: CCC(=O)c1cc2c(OC(C)=O)c3ccccc3c(OC(C)=O)c2o1]

TABLE 1-continued

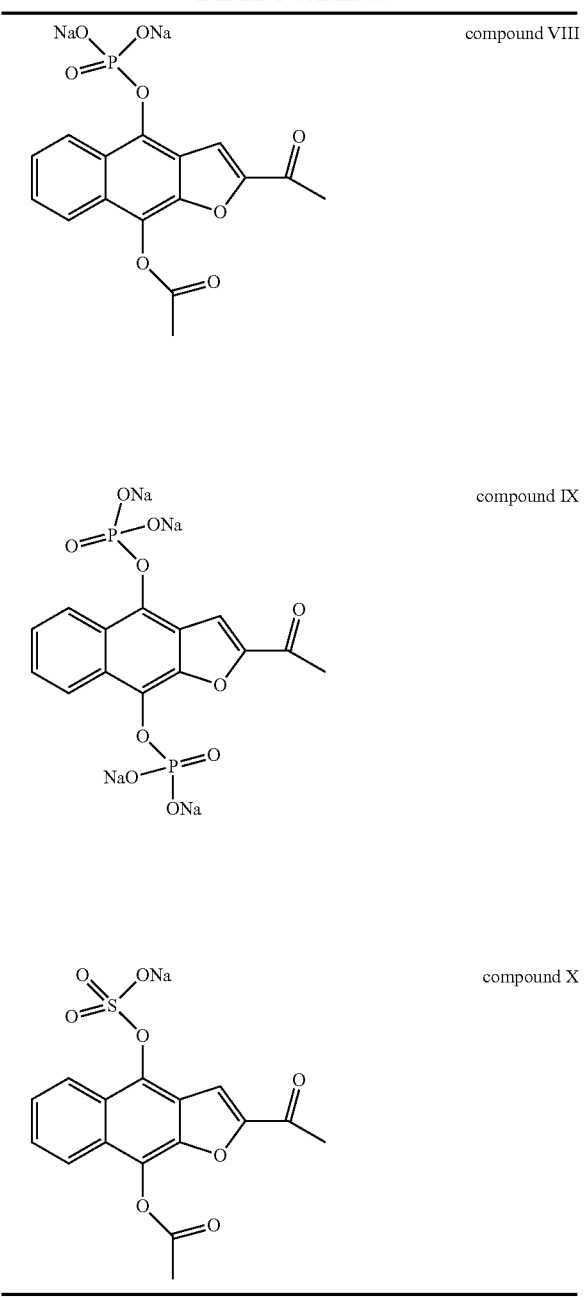

compound VIII compound IX compound X

In some embodiments, provided compounds are 4,9-bis(isobutoxy)-naphtho[2,3-b]furans. In some embodiments, provided compounds are 4,9-bis(pivaloxy)-naphtho[2,3-b]furans. In some embodiments, provided compounds are 4,9-bis(dichloroacetoxy)-naphtho[2,3-b]furans. In some embodiments, provided compounds are 4-acetoxy-9-hydroxy-naphtho[2,3-b]furans. In some embodiments, provided compounds are 4-hydroxy-9-acetoxy-naphtho[2,3-b]furans. In some embodiments, provided compounds are 4,9-bis{[(tert-butoxycarbonyl)amino]acetoxy}-naphtho[2,3-b]furans. In some embodiments, provided compounds are 4-acetoxy-9-[(tert-butoxycarbonyl)amino]acetoxy-naphtho[2,3-b]furans. In some embodiments, provided compounds are 4-[(tert-butoxycarbonyl)amino]acetoxy-9-acetoxy-naphtho[2,3-b]furans. In some embodiments, provided compounds are 4-hydroxy-9-[(tert-butoxycarbonyl)amino]ac-etoxy-naphtho[2,3-b]furans. In some embodiments, provided compounds are 4-[(tert-butoxycarbonyl)amino]acetoxy-9-hydroxy-naphtho[2,3-b]furans. In some embodiments, provided compounds are 4-phosphoester-9-acetoxy-naphtho[2,3-b]furans. In some embodiments, provided compounds are 4,9-bis(phosphoester)-naphtho[2,3-b]furans. In some embodiments, provided compounds are 4-sulfate-9-acetoxy-naphtho[2,3-b]furans.

Synthesis

There are numerous reports about synthesis of naphtho[2,3-b]furan-4,9-diones (*J. of Natural Products*, 1982, 45: 600-604; *Heterocycles*, 1999, 51: 497-500; US 2006/0142271; WO 2009036059; *Bioscience, Biotechnology, and Biochemistry*, 2006, 70: 1009-1012; *J. Chem. Soc.*, 1971, C: 153; *Tetrahedron*, 1974, 30: 3193; *An. Acad. Bras. Cienc.*, 1990, 62: 329; *J. Hererocyclic Chem.*, 1994, 31: 1303-1304; *Canadian Journal of Chemistry*, 1974, 52: 88-94; *Synthesis*, 1979, 3: 188-189; *Chemistry Letters*, 1988, 8: 1415-1418; *British Journal of Haematology*, 2005, 131: 520-529). When the substituent group at position 2 is, for example, alkylcarbonyl or arylcarbonyl, synthesis of naphtho[2,3-b]furan-4,9-diones can be carried out as reported (*Heterocycles*, 1999, 51: 497-500) which is shown in scheme 1.

Scheme 1:

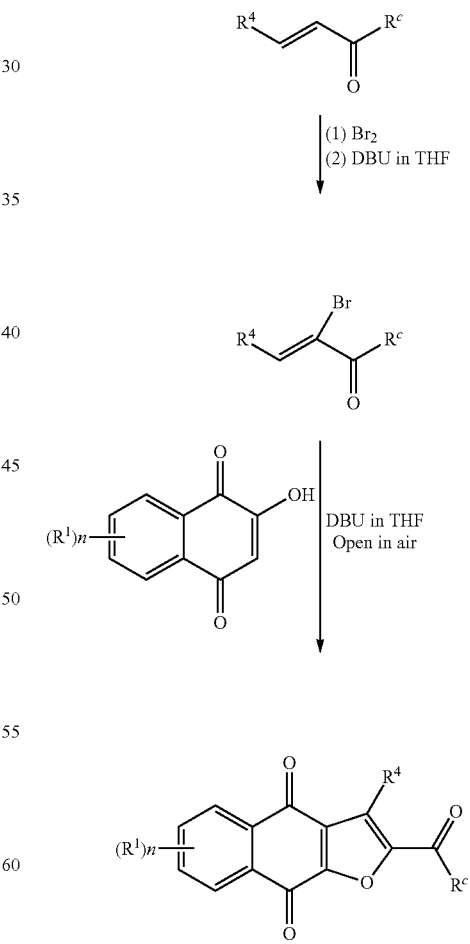

wherein DBU is 1,8-Diazabicyclo[5.4.0]undec-7-ene, THF is tetrahydrofuran, and $R^1$, $R^4$, $R^c$, and n are as defined and described herein.

The method shown in scheme 1 has been modified to facilitate large scale preparation and to avoid undesired byproduct naphtho[2,3-b]dihydrofuran-4,9-diones. The modified method is described as scheme 2.

Scheme 2:

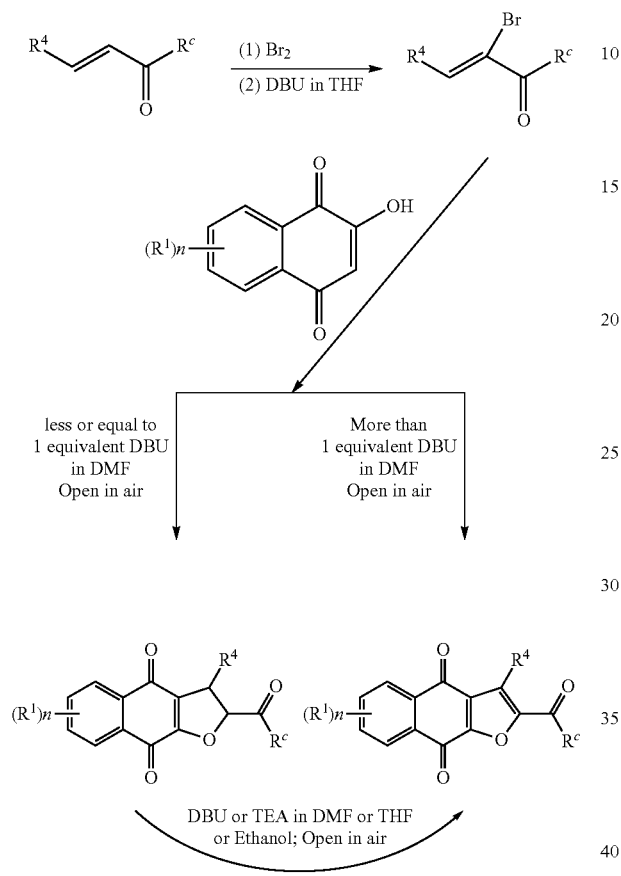

wherein DMF is N,N-dimethylformamide, TEA is triethylamine, DBU and THF are described in scheme 1, and $R^1$, $R^4$, $R^c$, and n are as defined and described herein.

In scheme 2, use of high boiling point solvent is favorable in large scale preparation in open air for safety consideration. In some embodiments, the high boiling solvent has a boiling point greater than 100° C. In certain embodiments, the solvent is N,N-dimethylformamide or dimethyl sulfoxide. In some embodiments, the solvent is not toluene. As shown in scheme 2, a naphthodihydrofurandione (e.g., 2-alkylcarbonyl-naphtho[2,3-b]dihydrofuran-4,9-dione) was also prepared and purified in satisfactory yield, and was converted into a naphthofurandione (e.g., 2-alkylcarbonyl-naphtho[2,3-b]furan-4,9-dione) with quantitative yield using a suitable base in open air. In some embodiments, the suitable base is a tertiary amine. In some embodiments, the suitable base is DBU. In some embodiments, the suitable base is TEA. This elucidates the mechanism of the final reaction step shown in scheme 1 and helps to eliminate the undesired dihydrofuran byproduct in the one pot synthesis by adding extra base such DBU or TEA.

Exemplary naphotho[2,3-b]furan-4,9-dione compounds are set forth in Table 2 below.

TABLE 2

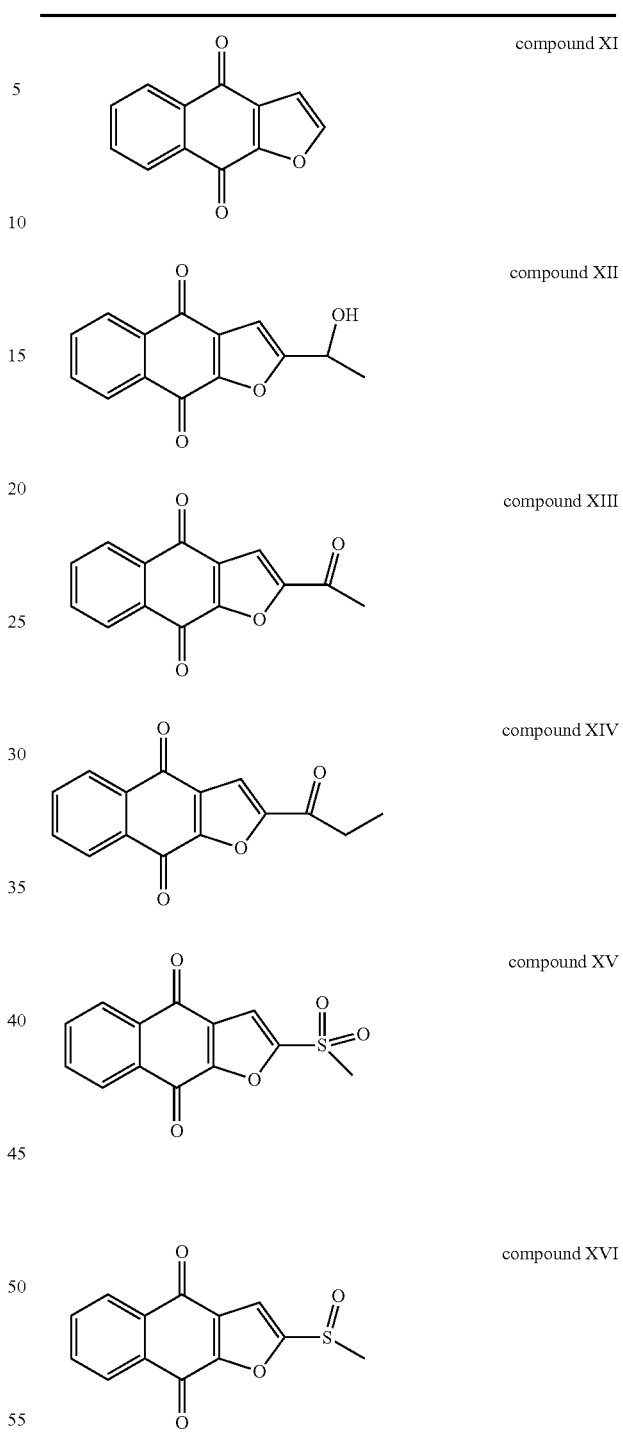

Synthesis of the compounds listed in Table 2 is described in the exemplification section. Among all compounds listed in Table 2, only compound XIII and XIV are synthesized as described in Scheme 2.

When either $R^2$ or $R^3$ or both of them are —C(=O)$R^c$, synthesis of the compound of formula I is carried out as described in scheme 3 using a naphtho[2,3-b]furan-4,9-dione or a derivative of a 4,9-dihydroxy-naphtho[2,3-b]furan as one of starting materials.

Scheme 3:

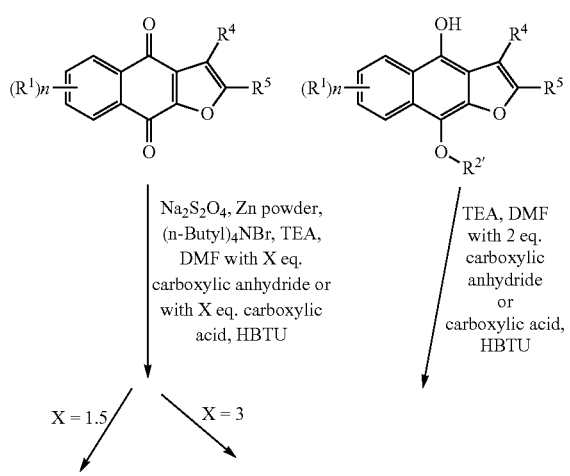

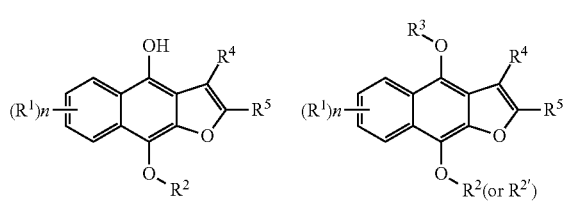

wherein TEA is triethylamine; HBTU is N,N,N',N'-tetramethyl-O-(1H-benzotriazol-1-yl)uronium hexafluorophosphate; DMF is as defined in scheme 2.

When either $R^2$ or $R^3$ or both of them are —P(=O)$OR^aOR^b$, synthesis of the compound of formula I is carried out as described in scheme 4 using a naphtho[2,3-b]furan-4,9-dione or a derivative of a 4,9-dihydroxy-naphtho[2,3-b]furan as one of starting materials.

Scheme 4:

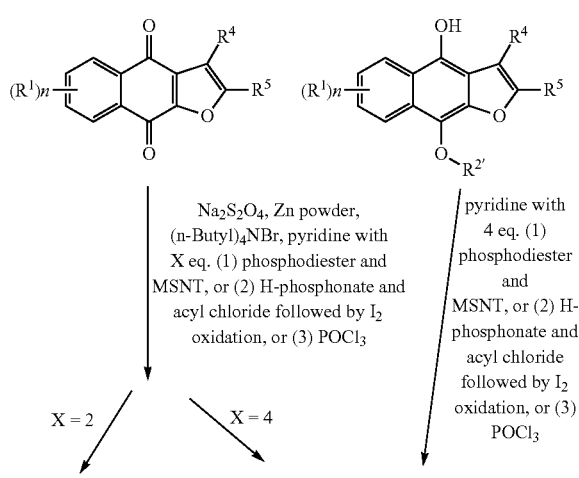

wherein MSNT is 1-(2-Mesitylenesulfonyl)-3-nitro-1H-1,2,4-triazole; acyl chloride is pivaloyl chloride.

When either $R^2$ or $R^3$ or both of them are —S(=O)$_2OR^a$, synthesis of the compound of formula I is carried out as described in scheme 5 using a naphtho[2,3-b]furan-4,9-dione or a derivative of a 4,9-dihydroxy-naphtho[2,3-b]furan as one of starting materials.

Scheme 5:

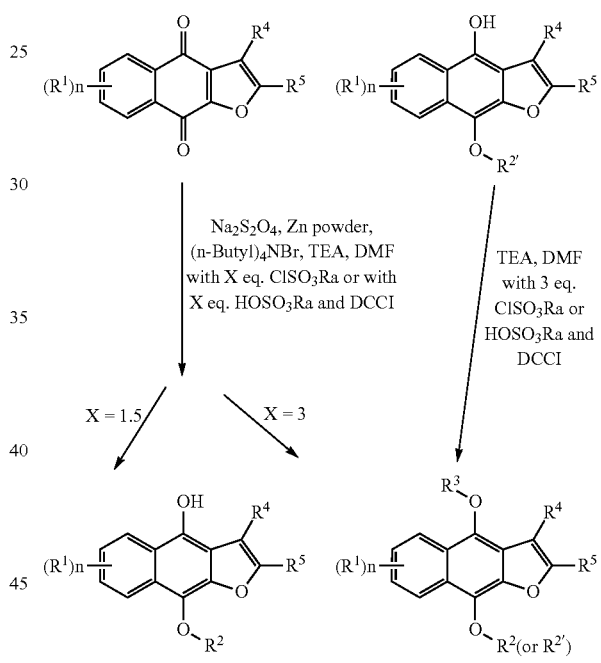

wherein DCCI is dicyclohexyl carbodiimide; TEA and DMF are as defined in scheme 3.

The Therapeutically Active Chemical Species In vivo

Naphtho[2,3-b]furan-4,9-diones are readily reduced by sodium hydrosulfite (Koyanagi J, et al. *J. Heterocyclic Chem.* 1997, 34: 407-412; and our unpublished data). A DMSO solution of compound XI, XIII, XV, or XVI was mixed with excessive sodium hydrosulfite aqueous solution. Analysis of each mixture with HPLC showed that the reduced 4,9-dihydroxy-naphtho[2,3-b]furan product is varied in stability. In the HPLC chromatographys shown in FIG. 1, there are bumpy areas between the peaks of 4,9-dihydroxy-naphtho[2,3-b]furans and the peaks of naphtho[2,3-b]furan-4,9-diones except for the one from compound XI mixture. The bumpy areas indicate oxidation of 4,9-dihydroxy-naphtho[2,3-b]

furans by oxygen into corresponding naphtho[2,3-b]furan-4,9-diones during the HPLC resolving process.

Either in vivo or in vitro, compounds of formula I can be degraded by esterases or other proteins or some nucleophilic small molecules into 4,9-dihydroxy-naphtho[2,3-b]furans. However, as demonstrated in the sodium hydrosulfite reduction reaction (FIG. 1), 4,9-dihydroxy-naphtho[2,3-b]furans can be oxidized by oxygen into corresponding naphtho[2,3-b]furan-4,9-diones. Scheme 6 below showed chemical conversion of a compound of formula I in in vitro biological fluid such as human plasma.

(Danson S, et al. *Cancer Treatment Review*, 2004, 30: 437-449). β-lapachone, the naturally occurring naphthoquinone, acts against cancer cells with assistance from NQ01 in the cancer cells (Pink J J, et al. *The Journal of Biological Chemistry*, 2000, 275:5416-5424; Bey E A, et al. *Proc. Natl. Acad. Sci. USA*, 2007, 104:11832-11837). In cancer cells, β-lapachone undergoes the intracellular NQ01 catalyzed futile redox cycles during which the harmful reactive oxygen species (ROS) is generated and thus kills the cancer cells. Without wishing to be bound by theory, it is believed that the Scheme 6:

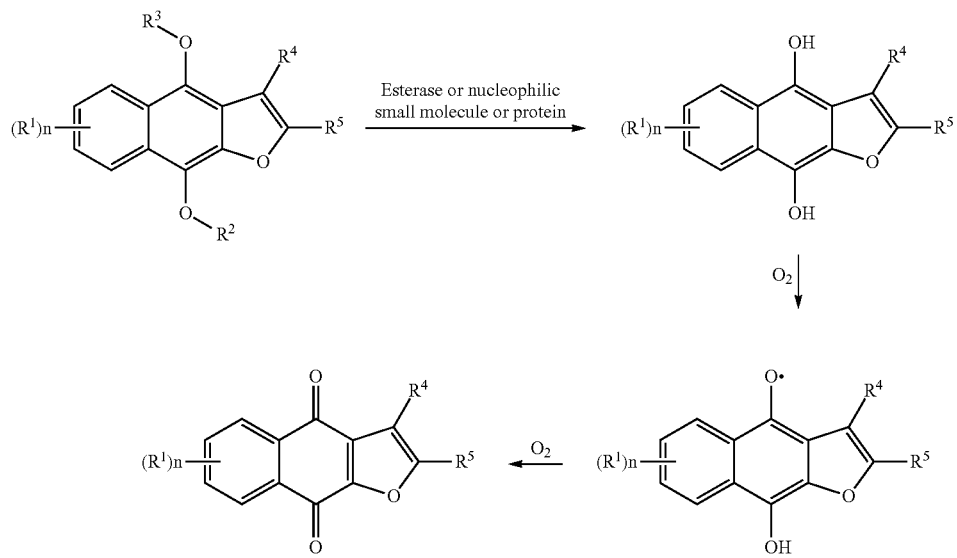

Figure 2:
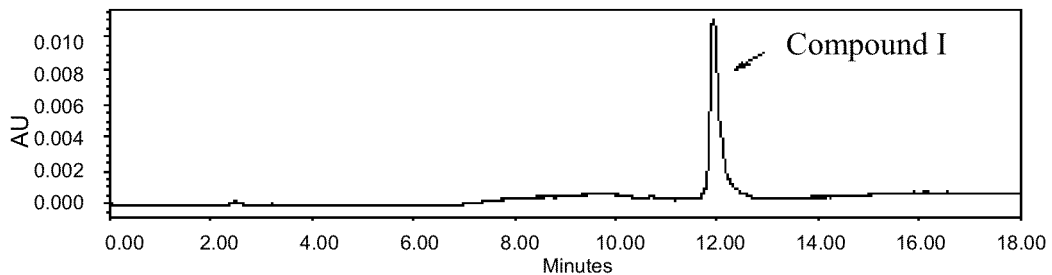
FIG. 2. HPLC chromatography of the exemplary ester of 4,9-dihydroxy-naphtho[2,3-b]furan and its human plasma incubated mixtures. Before HPLC analysis, proteins in the human plasma incubated mixtures were removed by addition of 9 times volume of acetonitrile and then centrifuging.
Figure 2:
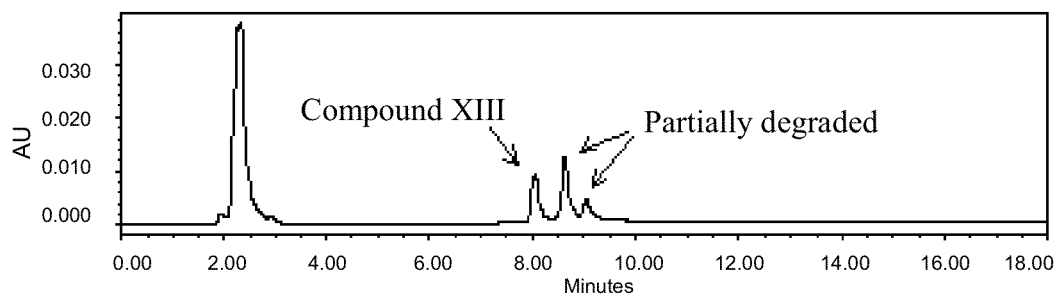
Figure 2:
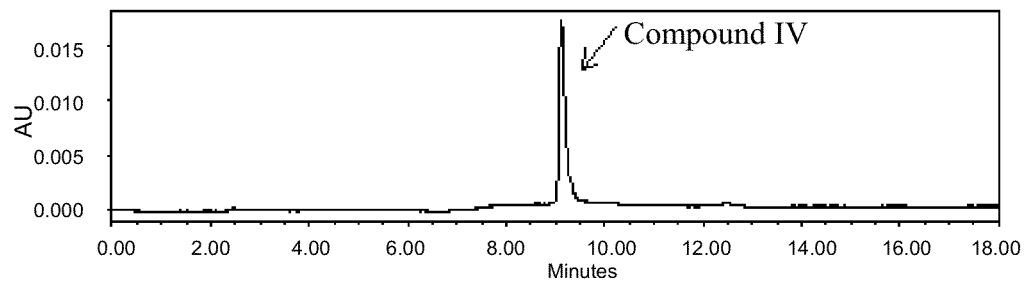
Figure 2:
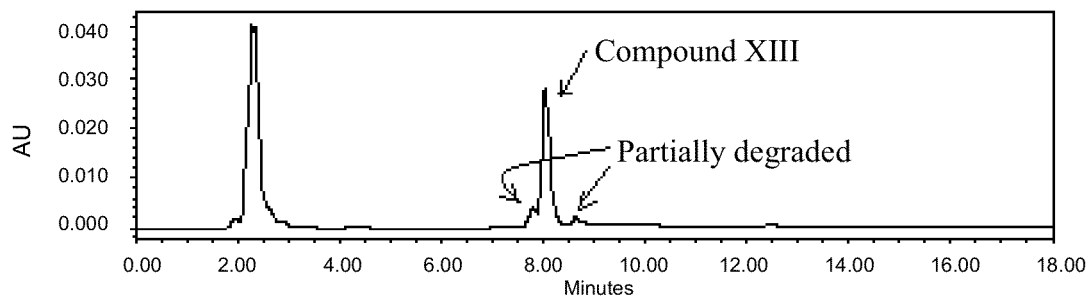
Figure 2:
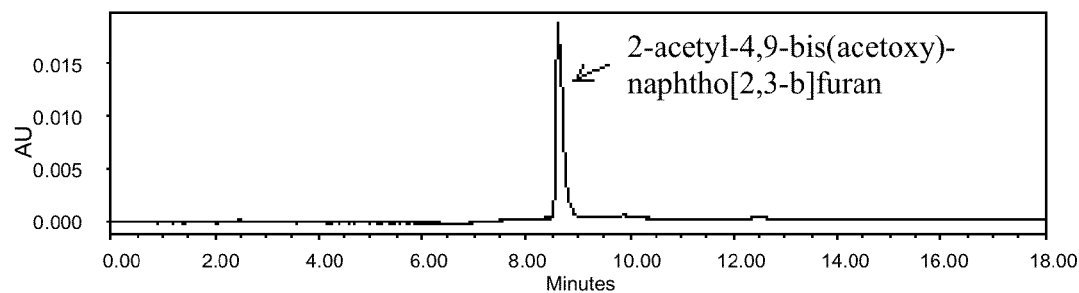
Figure 2:
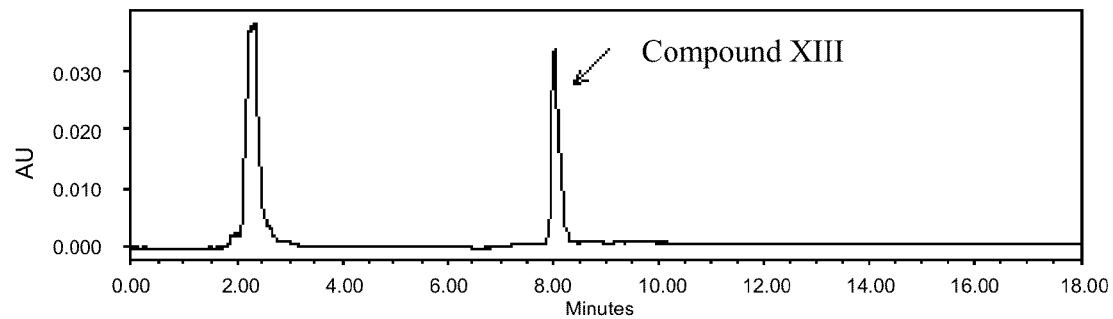

The compounds of formula I were incubated in human plasma at 37° C. for 2 hours, and then the mixtures were treated with acetonitrile to remove protein and the resulting supernatants were analyzed by HPLC (FIG. 2). For the incubation of 2-acetyl-4,9-bis(acetoxy)-naphtho[2,3-b]furan, the only detectable product was compound XIII; for compound I and IV, the detectable products were compound XIII and partially degraded products. However, compound II is barely degraded under the same conditions due to stereo hindrance (data not shown here). Without wishing to be bound by a particular theory, it is believed that, although not detected due to instability in a protein-free environment, the direct hydrolysis product of a compound of formula I, 4,9-dihydroxy-naphtho[2,3-b]furan, and its partially oxidized product semihydroquinone (shown in scheme 6) co-exist in vivo and play important biological roles.

First, quinone compounds are redox capable and can exist in vivo as several chemical species. Coenzyme Q10 is one of a few quinone compounds with fully identified chemical species profile in vivo (Bhagavan H N, et al. *Mitochondrion*, 200, 7S: S78-S88). The circulating coenzyme Q10 in a human is almost entirely in the form of hydroquinone (or quinol) (Craft N E, et al. *FASEB J.* 2005, 19, A449; Bhagavan H N, et al. *Int. J. Pharmaceut.* 2007, 333: 112-117; Mohr D, et al. *Redox Rep.* 1999, 4: 79-87). Some other quinone compounds, like Mitomycin C, E09, and AZQ, are converted in vivo by a reaction catalyzed by NQ01 (or DT-diaphorase) into their corresponding hydroquinones where their alkylation function groups are activated and thus they act against cancer cells reduced forms of the anticancer agents, Mitomycin C, E09, AZQ, and β-lapachone, are the therapeutically active chemical species.

Like other quinone compounds mentioned above, naphtho[2,3-b]furan-4,9-diones are also chemically active in vivo and are good substrates of the reduction enzymes such as NQ01, cytochrome b5 and P450 reductase (unpublished observation). However, there is no report which discusses either the general relationship between their chemical conversions and their biological activities or even only the chemical conversion in vivo.

Figure 3:
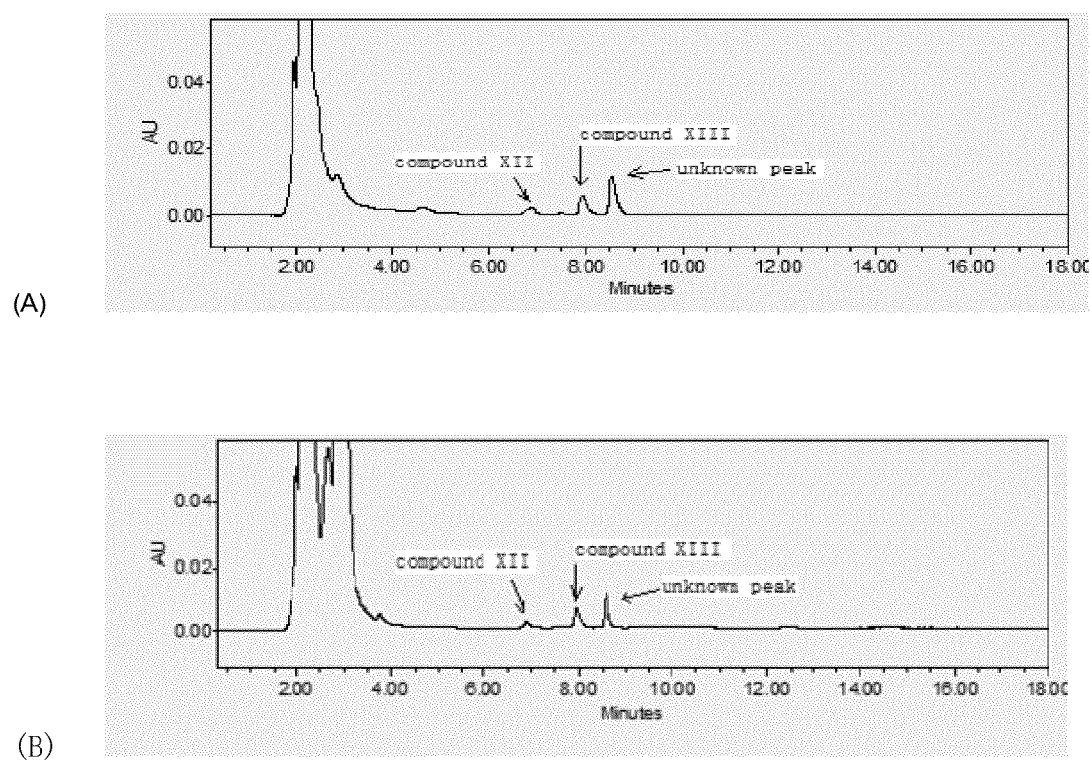
FIG. 3. Identification of compound XII as one of the metabolites of compound I and XIII in vivo or in vitro, time course and interfering factor of compound XII formation in human whole blood. (A) HPLC chromatography of mouse plasma. The mouse was orally gavage fed with amorphous solid of compound XIII at dosage of 200 mg/kg, then blood was drawn 2 hours later; (B) HPLC chromatography of mouse plasma. The mouse was orally gavage fed with amorphous solid of compound I at dosage of 100 mg/kg, then blood was drawn 1 hours later; (C) Time course of compound XII formation in the 37° C. incubation mixture of 20 μM compound XIII in human whole blood; (D) Relative amount of compound XII and XIII when 20 μM compound XIII and different concentration of β-lapachone were incubated in human whole blood at 37° C. for 30 minutes.
Figure 3:
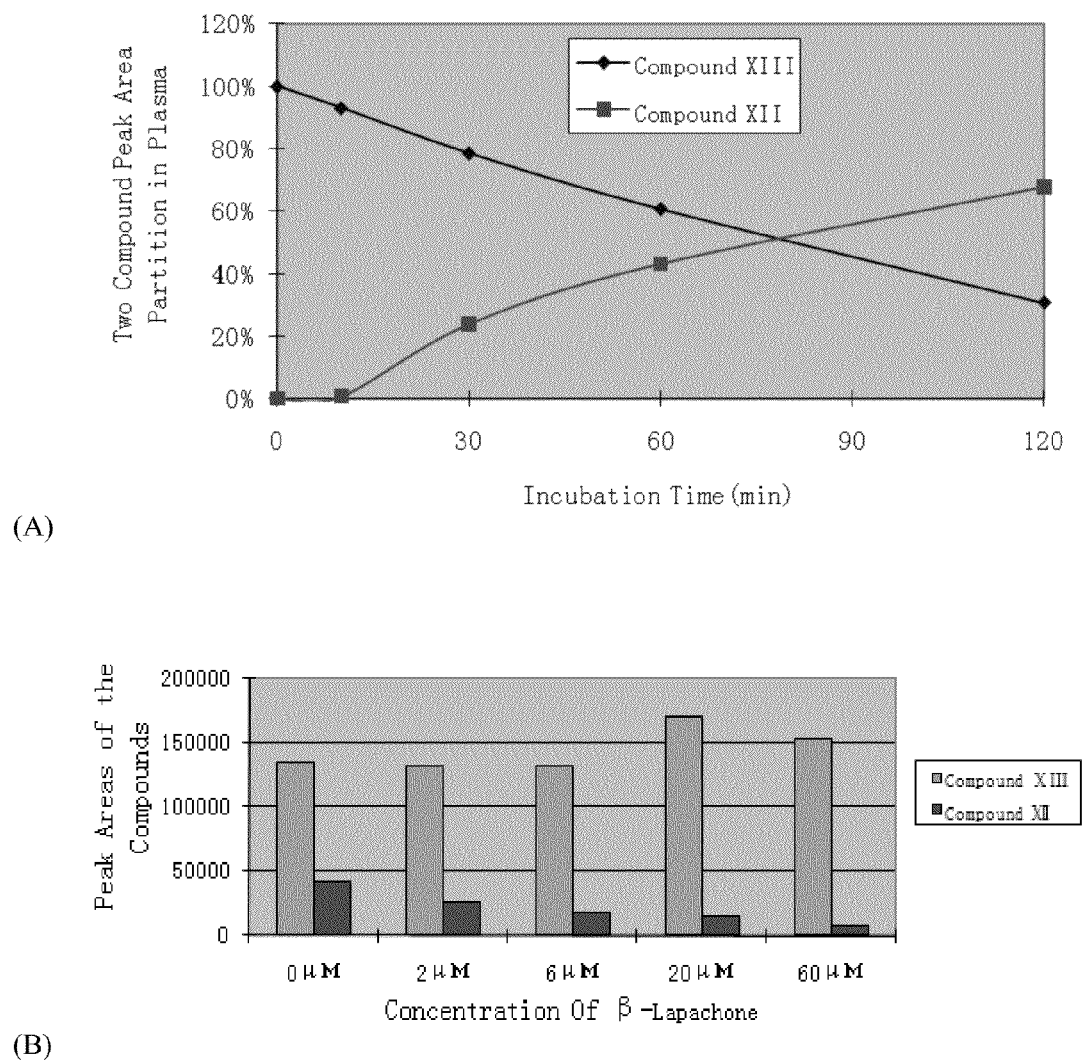

Second, a major metabolite found after incubation of compound I, III, IV, VI or XIII in biological fluid, such as human whole blood, or cancer cell lysate, or liver microsomes, or mouse oral uptake system, is compound XII (FIG. 3). Similarly, a major metabolite found after incubation of compound V, VII or XIV in biological fluid is 2-(1-hydroxy-n-propyl)-naphtho[2,3-b]furan-4,9-dione (data not shown). Reduction of the position 2 substituent carbonyl group is part of quinone redox reaction as evidenced by the β-lapachone effect on the formation of compound XII in the compound XIII incubation mixture of human whole blood (part D of FIG. 3). The possible reaction mechanism is proposed as shown in scheme 7, in which the two electron reduction could be NQ01 catalyzed reduction or two successive cytochrome b5 reductase or p450 reductase catalyzed reaction. As substrate of these enzymes, β-lapachone could compete for the two electron or single electron reaction and thus reduced formation of the metabolism product.

Scheme 7:

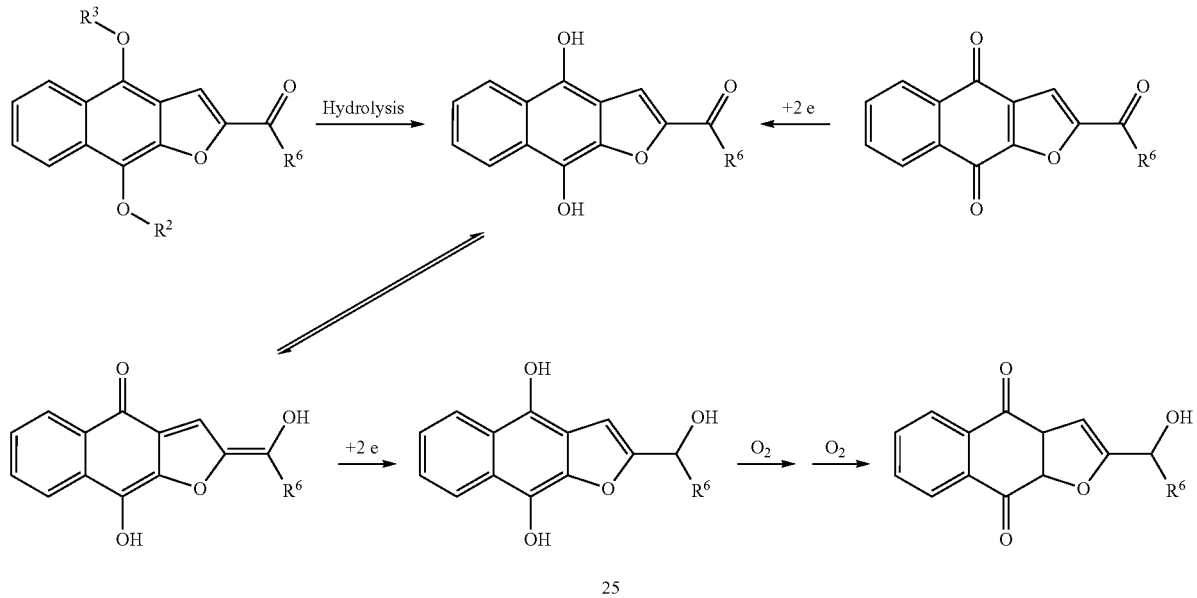

Figure 4:
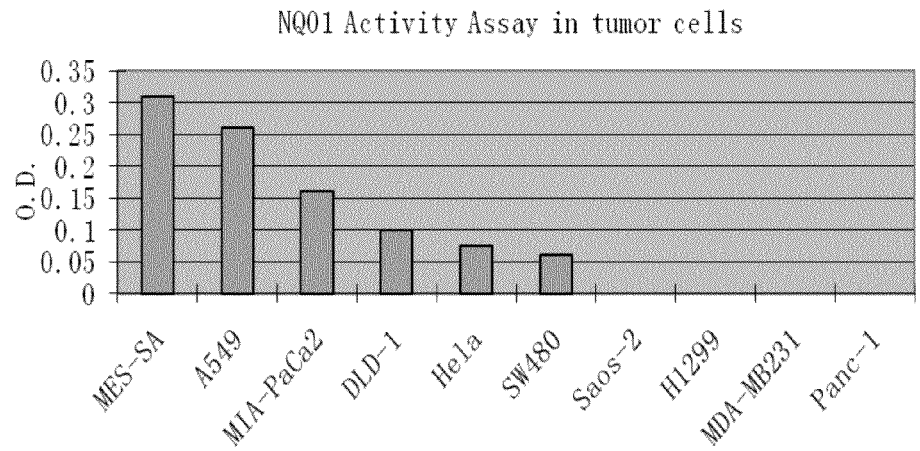
FIG. 4. Dicumarol (NQO1 inhibitor, Riley R J, et al. *Biochem. Pharmacol.* 1992, 43: 1657-1669; Ross D, et al. *Cancer Metastasis Rev.* 1993, 12: 83-101) effect on compound biological activity.
Figure 4:
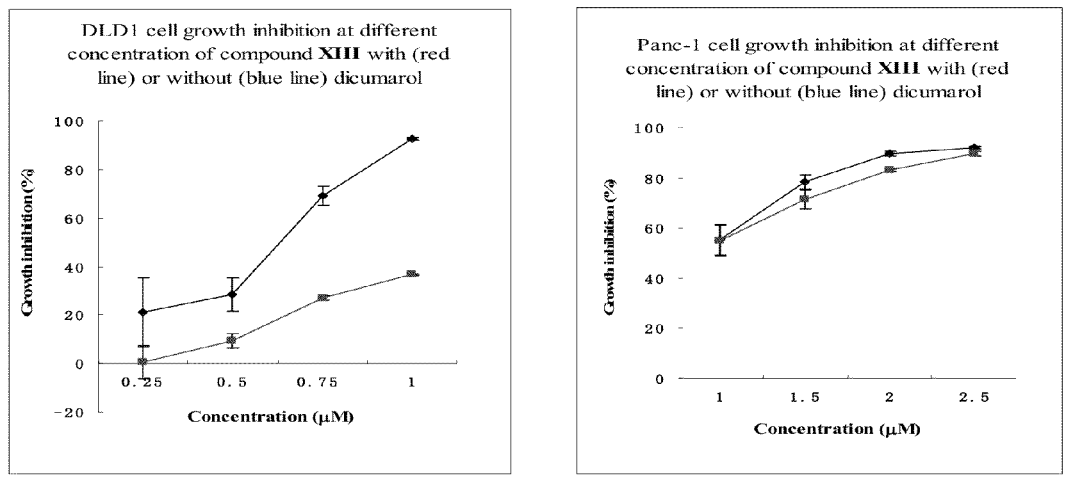
Figure 4:
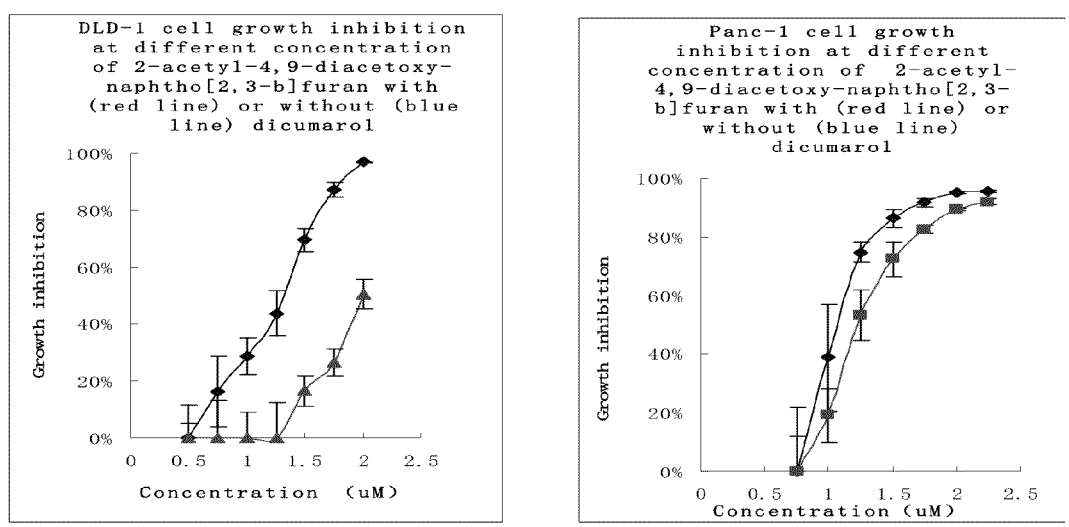

Third, NQ01 plays an important role in biological activity of naphtho[2,3-b]furan-4,9-diones (FIG. 4). NQ01 catalyzes obligatory two-electron reduction of quinone and is an important detoxifying enzyme (Riley R J, et al. *Biochem. Pharmacol.* 1992, 43: 1657-1669; Ross D, et al. *Cancer Metastasis Rev.* 1993, 12: 83-101). NQ01 enzymetic activity can be specifically inhibited by dicumarol (Traver R D, et al. *British Journal of Cancer,* 1997, 75: 69-75). As shown in FIG. 4, dicumarol attenuates anticancer activities of 2-acetyl-4,9-diacetoxy-naphtho[2,3-b]furan and compound XIII when the treated cancer cells (for example, DLD1) have significant NQ01 enzymatic activity. In opposite, dicumarol showed little effect when the treated cancer cells (for example, Panc-1) have no significant NQ01 enzymatic activity. Similar dicumarol effect was observed on anticancer activity of the compounds of formula I and other naphtho[2,3-b]furan-4,9-diones (data not shown).

Figure 5:
FIG. 5. The fluorescence pictures of DLD1 cells after treatment with 40 μM dichlorofluorescin diacetate (DCFH-DA) and followed with 0.3 μM test compound, or 100 μM hydrogen peroxide, or DMSO only (control). The pictures were taken with a fluorescence microscope (Olympus IX70 Inverted) in which the excitation filter was set at 488 nm and the emission filter at 530 nm.
Figure 5:
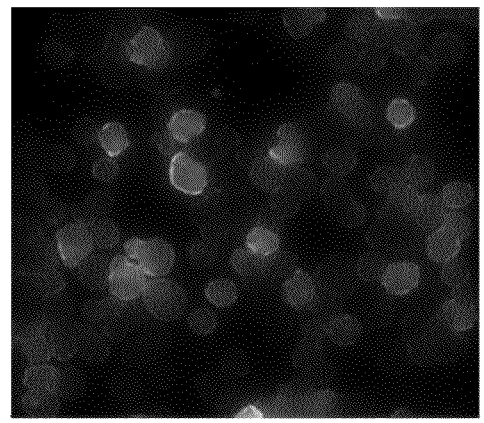
Figure 5:
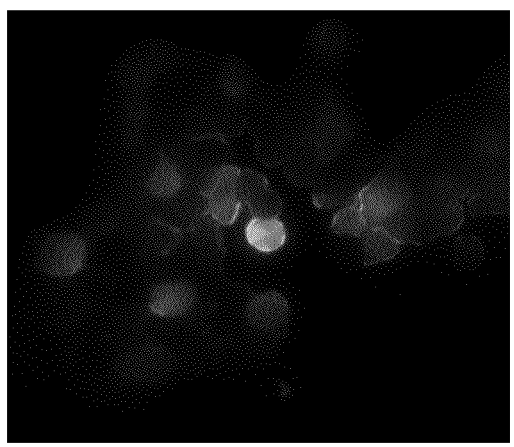
Figure 5:
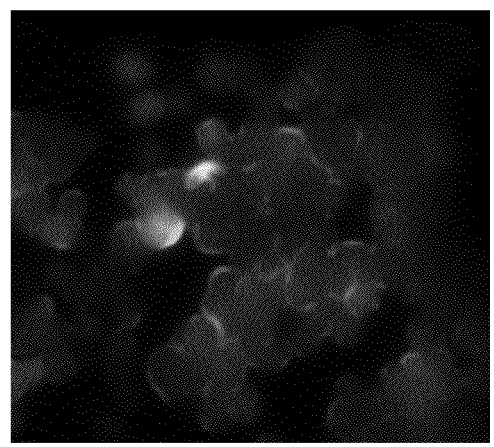
Figure 5:
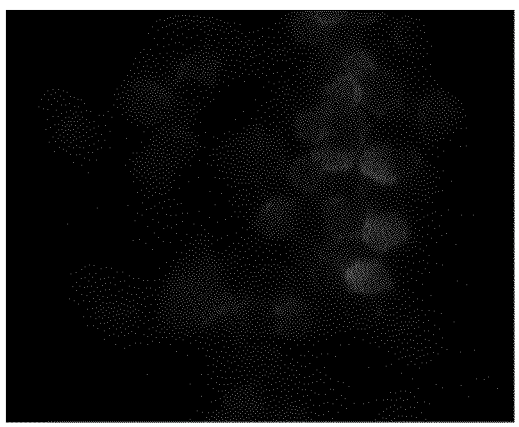
Figure 5:
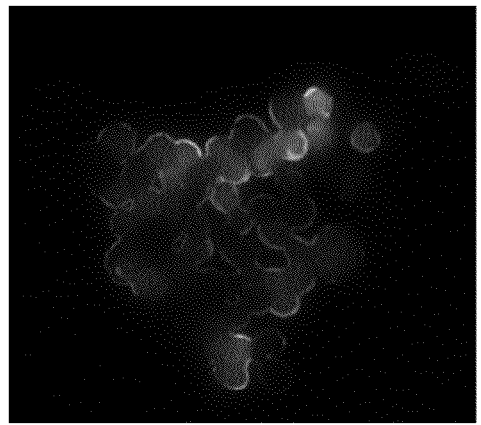

Fourth, the compounds of formula I, their analogs and naphtho[2,3-b]furan-4,9-diones generate significant ROS in cancer cells as shown in FIG. 5. Reactive oxygen species (ROS) is a general name of the chemical species of the incompletely reduced oxygen. ROS include superoxide anion radical, hydrogen peroxide and hydroxyl radical. ROS may have broad therapeutic applications, especially on cancer (Trachootham D, et al. *Antioxidants & Redox Signaling,* 2008, 10: 1343-1374; Fruehauf J P, et al. *Clin Cancer Res* 2007, 13: 789-794; Pelicano H, et al. *Drug Resist Update* 2004, 7: 97-110; Huang P, et al. *Nature* 2000, 407: 390-395; Trachootham D, et al. *Nature Review* 2009, 8: 579-591). Under physiologic conditions, cells maintain redox homeostasis by controlling the proper balance between ROS generation and elimination. However, when the increase of ROS reaches a certain level, it may overwhelm the cellular antioxidant capacity and trigger the cell-death process. Therefore, cancer cells with higher basal ROS generation would be more dependent on the antioxidant system and more vulnerable to further oxidative stress-inducing agents. A further increase of ROS stress by using exogenous ROS-generating agents may preferentially increase ROS above the threshold level in cancer cells, leading to cell death.

In the dichlorofluorescin diacetate (DCFH-DA) pretreated cancer cells, further treatment with fractional micromole of a compound of formula I or naphtho[2,3-b]furan-4,9-dione for less than 30 minutes has similar effect to the treatment of 100 μM of hydrogen peroxide (FIG. 5).

Figure 6:
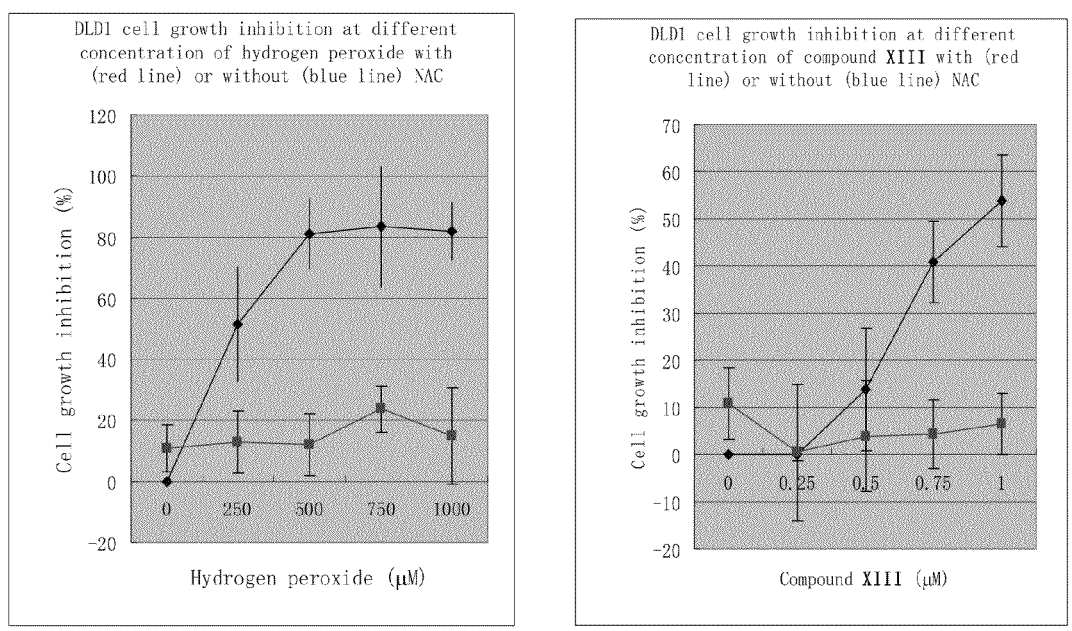
FIG. 6. Antioxidant N-acetyl-L-cysteine (NAC) effect on hydrogen peroxide or compound XIII induced toxicity to DLD1 cells.

Fifth, n-acetyl-L-cysteine (NAC) blocks anticancer activities of naphtho[2,3-b]furan-4,9-diones as shown in FIG. 6. NAC is one of effective ROS scavengers, reduces or blocks ROS induced cytotoxicity. The reaction possibility between NAC and compound XIII in culture medium had been ruled out by HPLC analysis.

Figure 7:
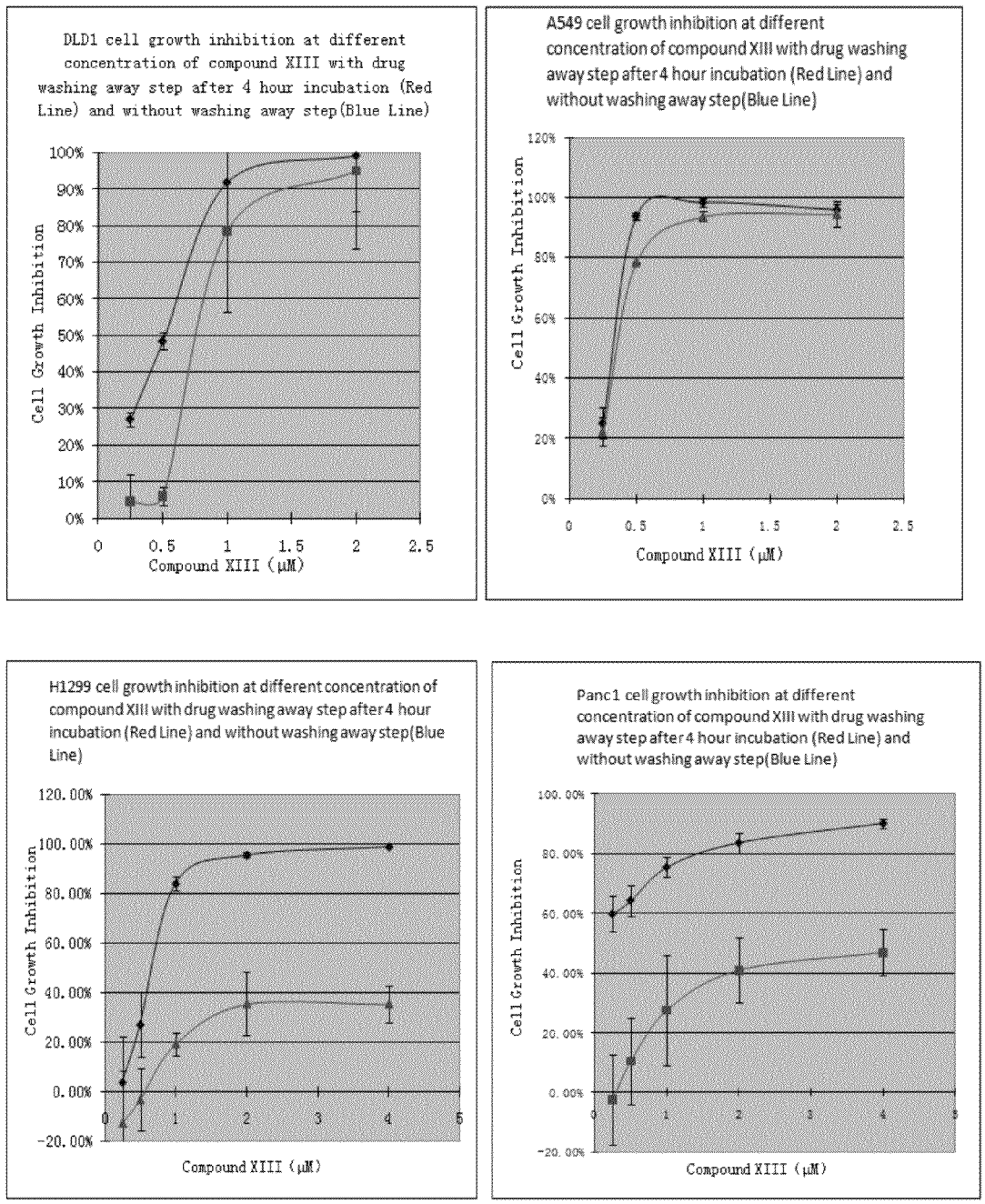
FIG. 7. Effect of compound XIII incubation time on cancer cell growth inhibition.

Finally, compound XIII shows fast cytotoxicity to the cancer cell lines with high NQ01 activity but not the cancer cell lines without NQ01 activity as shown in FIG. 7. Fast cytotoxicity means the damage caused by drug to cancer cell line in short time which is counted by hours, and the damage is sufficient to cause cell death in later time. ROS induced cytotoxicity is the typical fast cytotoxicity. DLD1 and A549 cell lines have significant NQ01 activity as shown in part A of FIG. 4, full time treatment or 4 hour treatment with compound XIII made no significant difference in cell growth inhibition. On the contrary, H1299 and Panc 1 cell lines have no NQ01 activity as shown in part A of FIG. 4, full time treatment with compound XIII caused much higher cell growth inhibition than 4 hour treatment.

4,9-Dihydroxy-naphtho[2,3-b]furans are unstable in protein free environment under aerobic condition, but exist in biological fluid and play important roles in the biological activity of the compounds of formula I and naphtho[2,3-b]furan-4,9-diones, as evidenced by: (1) redox reactions in vivo are common chemical properties among quinone and hydroquinone compounds and hydroquinones play important biological roles; (2) reduction of position 2 substituent carbonyl group to hydroxyalkyl group in compound I, III-VII, XIII and XIV is linked to quinone redox reaction, the precursor of the metabolite with position 2 substituent hydroxyalkyl group is likely 4,9-dihydroxy-naphtho[2,3-b]furan; (3) NQ01 catalyzes formation of 4,9-dihydroxy-naphtho[2,3-b]furan in chemistry and plays important role on biological activity of the compounds of formula I, their analogs and naphtho[2,3-b]furan-4,9-diones; (4) the compounds of formula I, their analogs and naphtho[2,3-b]furan-4,9-diones generate significant ROS in cancer cells; and (5) NAC effect and fast cytotoxicity confirm ROS role on biological activity of the compounds of formula I, their analogs and naphtho[2,3-b]furan-4,9-diones. Scheme 8 reasonably links NQ01, ROS generation and ROS biological roles together. The naphtho[2,3-b]furan-4,9-dione or the compound of formula I is reduced or hydrolyzed into therapeutically active hydroquinone (quinol), 4,9-dihydroxy-naphtho[2,3-b]furan. The therapeutically active quinol reduces oxygen to superoxide anion, and quinol itself is oxidized to semihydroquinone (semi-quinone) which reduces another oxygen molecule to superoxide anion, and the semi-quinone itself oxidized back to naphtho[2,3-b]furan-4,9-dione (quinone). The ROS generated by the NQ01 catalyzed futile redox cycle may overwhelm the cellular antioxidant capacity and trigger the cell-death process. Therefore, cancer cells with higher basal ROS level would be more dependent on the antioxidant system and more vulnerable to further oxidative stress-inducing agents, at mean time, cancer cells with higher NQ01 enzyme level further face higher ROS stress caused by NQ01 dependent exogenous ROS-generating agent. Without wishing to be bound by theory, it is believed that 4,9-dihydroxy-naphtho[2,3-b]furans are the therapeutically active compounds, and the compounds of formula I and naphtho[2,3-b]furan-4,9-diones are the prodrug of 4,9-dihydroxy-naphtho[2,3-b]furans.

Pharmaceutical Compositions

The present invention also provides pharmaceutical compositions comprising a compound of formula I and at least one pharmaceutically acceptable excipient or carrier or diluent.

As used herein, the pharmaceutically acceptable excipient or carrier or diluent is intended to include any and all solvents, dispersion media, coatings, antibacterial and antifungal agents, isotonic and absorption delaying agents, and the like, compatible with pharmaceutical administration. The pharmaceutically acceptable excipient or carrier or diluent including, but not limited to, water, saline solution, dextrose solution, triacetin, human albumin or its derivative, glycerol mono-(or di-)fatty acid esters, lecithin, phospholipids (such as phosphatidyl choline, phosphatidyl ethanolamine, phosphatidyl inositol, sphingomyelin, and the like), cholesterol, PEG-phospholipids, PEG-cholesterol, PEG-cholesterol derivatives, PEG-vitamin A, PEG-vitamin E, PEG-glycerol mono-(or di-)fatty acid esters, ethylene glycol mono-fatty acid esters, propylene glycol mono-fatty acid esters, 3-dialkyl(C1-8)amino-propylene glycol di-fatty acid esters, poly(ethylene glycol) mono-fatty acid esters, stearic acid, sorbitan esters, polyoxyethylene alkyl ethers, polyoxyethylene castor oil derivatives, polyoxyethylene sorbitan fatty acid esters, polyvinyl alcohol, polyvinylpyrrolidone, poloxamers; poloxamines, mixtures of sucrose stearate and sucrose distearate, ran- Scheme VIII:

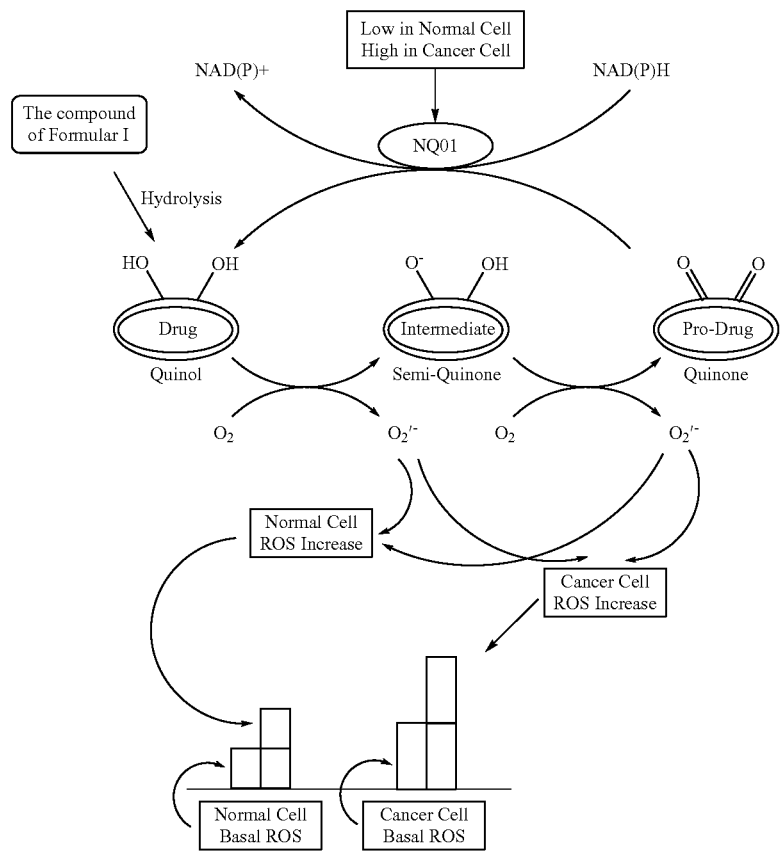

wherein quinol is hydroquinone, Semi-Quinone is semihydroquinone, Quinone is naphtho[2,3-b]furan-4,9-dione.

dom copolymers of vinyl acetate and vinyl pyrrolidone, deoxycholic acid, glycodeoxycholic acid, taurocholic acid, anionic biopolymers (such as casein or its derivative), anionic polymers, cationic biopolymers, salts of these acids (deoxycholic acid, glycocholic acid, glycodeoxycholic acid, taurocholic acid), the bulking agents, and mixtures thereof. The bulking agents includes starches or its derivatives, mannitol, lactose, maltitol, maltodextrin, maltose, dextrates, dextrin, dextrose, fructose, sorbitol, glucose, sucrose, carboxymethylcellulose, hydroxypropylcellulose, microcrystalline cellulose, ethylcellulose, methylcellulose, other suitable cellulose derivatives, gelatin, alginic acid, and its salt, colloidal silicon dioxide, croscarmellose sodium, crospovidone, magnesium aluminum silicate, povidone, benzyl phenylformate, chlorobutanol, diethyl phthalate, calcium stearate, glyceryl palmitostearate, magnesium oxide, poloxamer, polyvinyl alcohol, sodium benzoate, sodium lauryl sulfate, sodium stearyl fumarate, stearic acid, talc, zinc stearate, acacia, acrylic and methacrylic acid co-polymers, gums such as guar gum, milk derivatives such as whey, pharmaceutical glaze, glyceryl palmitostearate, hydrogenated vegetable oil, kaolin, magnesium carbonate, magnesium oxide, polymethacrylates, sodium chloride and mixtures thereof.

Formulations of the compound of formula I include those suitable for oral, nasal, topical (including buccal and sublingual), rectal, vaginal and/or parenteral administration. The formulation may conveniently be presented in unit dosage form and may be prepared by any methods well known in the art of pharmacy. The amount of active ingredient, which can be combined with a carrier material to produce a single dosage form, will generally be that amount of the compound which produces a therapeutic effect. Generally, out of 100%, this amount will range, for example, from about 1% to about 99% of active ingredient, from about 5% to about 70%, from about 10% to about 30%.

In some embodiments, the compound of formula I is formulated as emulsion suspension suitable for oral, nasal, topical (including buccal and sublingual), rectal, vaginal and/or parenteral administration. The emulsion suspension contains water immiscible organic solvent in which the compound of formula I is dissolved and aqueous solution and surface surfactant. In some embodiments, the water immiscible organic solvent in the emulsion suspension is triacetin. In some embodiments, the surface surfactant in the emulsion suspension is lecithin. In some embodiments, the aqueous solution in the emulsion suspension is saline.

Formulations of the compound of formula I suitable for oral administration may be in the form of capsules, pills, tablets, cachets, powders, granules, or as a solution or a suspension in an aqueous or non-aqueous or aqueous-organic solvent emulsion liquid, each containing a predetermined amount of a compound of formula I as an active ingredient.

In solid dosage forms of the compound of formula I for oral administration, the compound of formula I at a physical form of crystalline, micronized crystalline, nanoparticle, or amorphous form is mixed with one or more pharmaceutically acceptable excipient or carrier or diluent, such as glycerol mono-(or di-)fatty acid esters, lecithin, phospholipids (such as phosphatidyl choline, phosphatidyl ethanolamine, phosphatidyl inositol, sphingomyelin, and the like), cholesterol, PEG-phospholipids, PEG-cholesterol, PEG-cholesterol derivatives, PEG-vitamin A, PEG-vitamin E, PEG-glycerol mono-(or di-)fatty acid esters, ethylene glycol mono-fatty acid esters, propylene glycol mono-fatty acid esters, 3-dialkyl (C1-8)amino-propylene glycol di-fatty acid esters, poly(ethylene glycol) mono-fatty acid esters, stearic acid, sorbitan esters, polyoxyethylene alkyl ethers, polyoxyethylene castor oil derivatives, polyoxyethylene sorbitan fatty acid esters, polyvinyl alcohol, polyvinylpyrrolidone, poloxamers; poloxamines, mixtures of sucrose stearate and sucrose distearate, random copolymers of vinyl acetate and vinyl pyrrolidone, deoxycholic acid, glycodeoxycholic acid, taurocholic acid, anionic biopolymers (such as casein or its derivative), anionic polymers, cationic biopolymers, salts of these acids (deoxycholic acid, glycocholic acid, glycodeoxycholic acid, taurocholic acid), bulking agents, and mixtures thereof. Bulking agents includes starches or its derivatives, mannitol, lactose, maltitol, maltodextrin, maltose, dextrates, dextrin, dextrose, fructose, sorbitol, glucose, sucrose, carboxymethylcellulose, hydroxypropylcellulose, microcrystalline cellulose, ethylcellulose, methylcellulose, other suitable cellulose derivatives, gelatin, alginic acid and salts thereof, colloidal silicon dioxide, croscarmellose sodium, crospovidone, magnesium aluminum silicate, povidone, benzyl phenylformate, chlorobutanol, diethyl phthalate, calcium stearate, glyceryl palmitostearate, magnesium oxide, poloxamer, polyvinyl alcohol, sodium benzoate, sodium lauryl sulfate, sodium stearyl fumarate, stearic acid, talc, zinc stearate, acacia, acrylic and methacrylic acid co-polymers, gums such as guar gum, milk derivatives such as whey, pharmaceutical glaze, glyceryl palmitostearate, hydrogenated vegetable oil, kaolin, magnesium carbonate, magnesium oxide, polymethacrylates, sodium chloride and mixtures thereof.

In liquid or semi-liquid dosage forms of the compound of formula I for oral, nasal, topical, rectal, vaginal and parenteral administration, a compound of formula I is mixed with one or more pharmaceutically acceptable excipient or carrier or diluent as a solution or a nanoparticle suspension in an aqueous or non-aqueous or aqueous-organic solvent emulsion liquid or semi-liquid, each containing a predetermined amount of a compound of formula I as an active ingredient. In certain embodiments, pharmaceutically acceptable excipients, carriers, or diluents include, but are not limited to, water, saline solution, dextrose solution, triacetin, human albumin or its derivative, glycerol mono-(or di-)fatty acid esters, lecithin, phospholipids (such as phosphatidyl choline, phosphatidyl ethanolamine, phosphatidyl inositol, sphingomyelin, and the like), cholesterol, PEG-phospholipids, PEG-cholesterol, PEG-cholesterol derivatives, PEG-vitamin A, PEG-vitamin E, PEG-glycerol mono-(or di-)fatty acid esters, ethylene glycol mono-fatty acid esters, propylene glycol mono-fatty acid esters, 3-dialkyl(C1-8)amino-propylene glycol di-fatty acid esters, poly(ethylene glycol) mono-fatty acid esters, stearic acid, sorbitan esters, polyoxyethylene alkyl ethers, polyoxyethylene castor oil derivatives, polyoxyethylene sorbitan fatty acid esters, polyvinyl alcohol, polyvinylpyrrolidone, poloxamers; poloxamines, mixtures of sucrose stearate and sucrose distearate, random copolymers of vinyl acetate and vinyl pyrrolidone, deoxycholic acid, glycodeoxycholic acid, taurocholic acid, anionic biopolymers (such as casein or its derivative), anionic polymers, cationic biopolymers, salts of these acids (deoxycholic acid, glycocholic acid, glycodeoxycholic acid, taurocholic acid), bulking agents, and mixtures thereof. Bulking agents includes starches or its derivatives, mannitol, lactose, maltitol, maltodextrin, maltose, dextrates, dextrin, dextrose, fructose, sorbitol, glucose, sucrose.

Naphtho[2,3-b]furan-4,9-diones (e.g., 2-acetyl-naphtho[2,3-b]furan-4,9-dione and 2-(1-hydroxyethyl)-naphtho[2,3-b]furan-4,9-dione) and their analogs or derivatives tend to form highly crystalline solids. While the crystallinity of such compounds is useful for synthetic processes, it can hinder oral bioavailability. As a solution, we have discovered methods of preparing amorphous solids of naphtho[2,3-b]furan-4,9-diones and their analogs and derivatives; these methods are described herein in the Examples and Figures.

Uses

Figure 9:
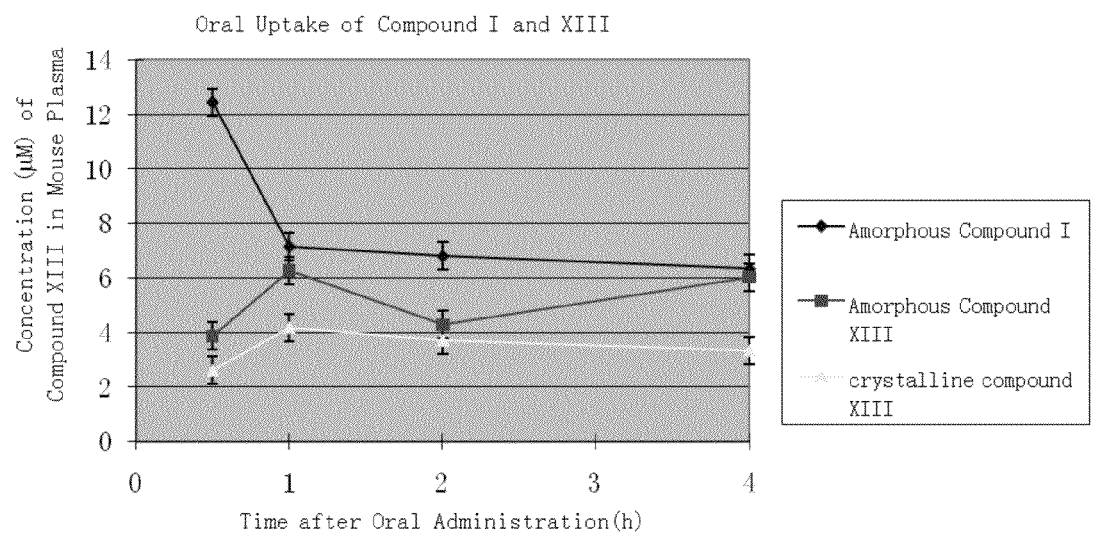
FIG. 9. Evaluation of oral uptakes of compound I and XIII with defined solid physical state. Concentrations of compound XIII in mouse plasma were obtained with HPLC analysis, every data point was average of three mouse plasma concentrations.
Figure 10:
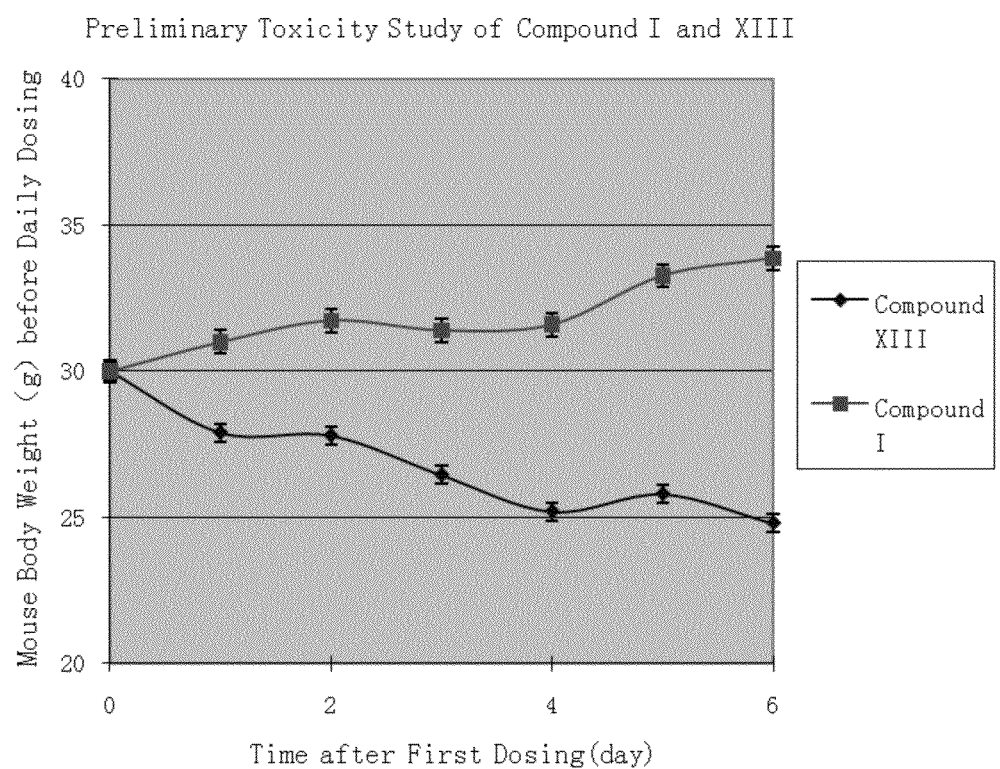
FIG. 10. Mouse body weight before daily dosing for one week. Three mice were orally gavage fed with amorphous solid of compound I at dose of 1,200 mg/kg or amorphous solid of compound XIII at dose of 800 mg/kg once daily.

Without wishing to be bound by theory, it is believed that the compounds of the present invention are prodrugs which will turns into therapeutically active dihydroxynapthofuran chemical species in vivo as discussed in the section of "The Therapeutically Active Chemical Species in vivo". In certain embodiments, compounds of formula I are more stable than the corresponding therapeutically active chemical species in vitro. In certain embodiments, compounds of formula I are of higher oral bioavailability than the corresponding quinone prodrugs (see FIG. 9). In certain embodiments, compounds of formula I display less toxicity than the corresponding quinone prodrugs (see FIG. 10).

Compounds of the present invention may be used in vitro or in vivo. In some embodiments, compounds of the present invention are provided for use in medicine. In some embodiments, the present invention provides methods of treating a subject suffering from or susceptible to a disease, disorder, or condition, the method comprising administering to the subject a therapeutically effective amount of a compound of formula I. In certain embodiments, compounds of formula I are useful in the treatment of proliferative diseases. However, inventive compounds described above may also be used in vitro for research or clinical purposes (e.g., determining the susceptibility of a patient's disease to a compound of formula I, researching the mechanism of action, elucidating a cellular pathway or process).

In some embodiments, the present invention provides a method of treating a subject suffering from or susceptible to a proliferative disease, disorder, or condition, the method comprising administering to the subject a therapeutically effective amount of a compound of formula I. In certain embodiments, the proliferative disease is a benign neoplasm. In certain embodiments, the proliferative disease is cancer. In certain embodiments, the proliferative disease is an inflammatory disease. In certain embodiments, the proliferative disease is an autoimmune disease. In certain embodiments, the proliferative disease is diabetic retinopathy.

Compounds of formula I may be used in the treatment of neoplasms. In certain embodiments, the neoplasm is a benign neoplasm. In other embodiments, the neoplasm is a malignant neoplasm.

In some embodiments, the present invention provides a method of treating a subject suffering from or susceptible to cancer, the method comprising administering to the subject a therapeutically effective amount of a compound of formula I. In some embodiments, the cancer is a hematological malignancy. In certain embodiments, the cancer is a solid tumor. Exemplary cancers that may be treated using compounds of formula I include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, nasopharyngeal cancer, gallbladder cancer, laryngeal cancer, oral cancer, penile cancer, glandular tumors, rectal cancer, small intestine cancer, head and neck cancer, multiple myeloma, colorectal carcinoma, kaposi sarcoma, ewing's sarcoma, osteosarcoma, leiomyosarcoma, glioma, meningioma, medulloblastoma, melanoma, urethral cancer, vaginal cancer, to name but a few.

In certain embodiments, compounds of formula I are useful for the treatment of diseases, disorders, and conditions of the brain, meninges, and the central nervous system. While not wishing to be bound by any particular theory, it is believed that compounds of formula I or their degraded product (therapeutically active chemical species) are capable of passing through the blood-brain barrier (BBB) and therefore can be useful to treat diseases, disorders, and conditions that require a systemically-administered therapeutic to pass through the BBB.

Hematological malignancies are types of cancers that affect the blood, bone marrow, and/or lymph nodes. Examples of hematological malignancies that may be treated using compounds of formula I include, but are not limited to: acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma.

Compounds of formula I may also be used to treated a refractory or relapsed malignancy. In certain embodiments, the cancer is a refractory and/or relapsed hematological malignancy. For example, the cancer may be resistant to a particular chemotherapeutic agent.

In some embodiments, the present invention provides a method of inhibiting or reducing cancer stem cell survival and/or self renewal with an effective amount of a compound of formula I.

Compounds of formula I may also be used to treat and/or kill cells in vitro or in vivo. In certain embodiments, a cytotoxic concentration of a compound of formula I is contacted with the cells in order to kill them. In some embodiments, a sublethal concentration of a compound of formula I is used to treat the cells. In certain embodiments, the concentration of a compound of formula I ranges from 0.1 nM to 100 µM. In certain embodiments, the concentration of a compound of formula I ranges from 0.01 µM to 100 µM. In certain embodiments, the concentration of a compound of formula I ranges from 0.1 µM to 50 µM. In certain embodiments, the concentration of a compound of formula I ranges from 1 µM to 10 µM. In certain embodiments, the concentration of a compound of formula I ranges from 1 µM to 10 µM, more particularly 1 µM to 5 µM.

Any type of cell may be tested or killed with a compound of formula I. Such cells may be derived from any animal, plant, bacterial, or fungal source, and may be at any stage of differentiation or development. In certain embodiments, cells are animal cells. In certain embodiments, cells are vertebrate cells. In certain embodiments, cells are mammalian cells. In certain embodiments, cells are human cells. Cells may be derived from a male or female human in any stage of development. In certain embodiments, cells are primate cells. In other embodiments, cells are derived from a rodent (e.g., mouse, rat, guinea pig, hamster, gerbil). In certain embodiments, cells are derived from a domesticated animal such as a dog, cat, cow, goat, pig, etc. Cells may also be derived from a genetically engineered animal or plant, such as a transgenic mouse.

Cells used in accordance with the present invention may be wild type or mutant cells, and may be genetically engineered. In certain embodiments, cells are normal cells. In certain embodiments, cells are hematological cells. In certain embodiments, cells are white blood cells. In certain particular embodiments, cells are precursors of white blood cells (e.g., stem cells, progenitor cells, blast cells). In certain embodiments, cells are neoplastic cells. In certain embodiments, cells are cancer cells. In certain embodiments, cells are derived from a hematological malignancy. In other embodiments, cells are derived from a solid tumor. For example, cells may be derived from a patient's tumor (e.g., from a biopsy or surgical excision). In certain embodiments, cells are derived from a blood sample from the subject or from a bone marrow biopsy. In certain embodiments, cells are derived from a lymph node biopsy. Such testing for cytotoxicity may be useful in determining whether a patient will respond to a particular combination therapy. Such testing may also be useful in determining the dosage needed to treat the malignancy. This testing of the susceptibility of a patient's cancer to a compound of formula I would prevent the unnecessary administration of drugs with no effect to the patient. The testing may also allow the use of lower dose of a compound of formula I if the patient's cancer is particularly susceptible to the compound of formula I.

In certain embodiments, cells are derived from cancer cells lines. For example, in certain embodiments, cells are hematopoietic progenitor cells such as $CD34^+$ bone marrow cells. In certain embodiments, cells are A549, DLD1, SW480, LOVO, HT-29, U-20S, MES-SA, SK-MEL-28, Panc-1, DU-145, CNE, U251, Eca-109, MGC80-3, SGC-7901, QGY-7701, BEL-7404, PLC/PRF/5, Huh-7, MOLT-3 (acute lymphoblastic T-cell), SKNLP (neuroblastoma), PC9 (adenocarcinoma), H1650 (adenocarcinoma), H1975 (adenocarcinoma), H2030 (adenocarcinoma), H3255 (adenocarcinoma), TC71 (Ewing's sarcoma), HTP-15 (glioblastoma), A431 (epithelial carcinoma), HeLa (cervical adenocarcinoma), or WD0082 (well-differentiated liposarcoma) cells. In certain embodiments, cell lines are resistant to a particular chemotherapeutic agent.

In some embodiments, the present invention provides a method of treating a subject suffering from or susceptible to obesity or an obesity-related disorder or condition, the method comprising administering to the subject a therapeutically effective amount of a compound of formula I.

In some embodiments, the present invention provides a method of treating a subject suffering from or susceptible to diabetes, the method comprising administering to the subject a therapeutically effective amount of a compound of formula I.

In some embodiments, the present invention provides a method of treating a subject suffering from or susceptible to a metabolic disease, disorder, or condition, the method comprising administering to the subject a therapeutically effective amount of a compound of formula I.

In some embodiments, the present invention provides a method of treating a subject suffering from or susceptible to a degenerative disease, disorder, or condition, the method comprising administering to the subject a therapeutically effective amount of a compound of formula I.

In some embodiments, the present invention provides a method of treating a subject suffering from or susceptible to a disease, disorder, or condition associated with mitochondrial dysfunction, the method comprising administering to the subject a therapeutically effective amount of a compound of formula I.

In some embodiments, the present invention provides a method of treating a subject suffering from or susceptible to a cardiovascular disease, disorder, or condition, the method comprising administering to the subject a therapeutically effective amount of a compound of formula I. In some embodiments, the disease, disorder, or condition is selected from the group consisting of hypertension, congestive heart failure, heart attack, hypertensive heart disease, atherosclerosis, coronary artery disease, angina, ischemia, ischemic stroke.

In some embodiments, compound of formula I may be useful to treat other diseases, disorders, or conditions as described in WO 2009/036059 and WO 2006/088315, the entire contents of each of which are hereby incorporated by reference.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In certain embodiments, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabine, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see The Merck Manual, Eighteenth Ed. 2006, the entire contents of which are hereby incorporated by reference.

In certain embodiments, inventive compounds are useful in treating a subject in clinical remission. In some embodiments, the subject has been treated by surgery and may have limited unresected disease.

If desired, the effective daily dose of the active compound may be administered as two, three, four, five, six, or more sub-doses administered separately at appropriate intervals throughout the day, optionally, in unit dosage forms.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In some embodiments, a chronic treatment involves administering a compound or pharmaceutical composition of the invention repeatedly over the life of the subject. In some embodiments, chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In certain embodiments, a therapeutically effective amount of a compound of formula I is from about 1 mg/m$^2$ to about 5,000 mg/m$^2$ (I.V.) or from about 1 mg/m$^2$ to about 50,000 mg/m$^2$ (PO). In certain embodiments, a therapeutically effective amount of a compound of formula I is from about 2 mg/m$^2$ to about 3,000 mg/m$^2$ (I.V.) or from about 10 mg/m$^2$ to about 30,000 mg/m$^2$ (PO).

In certain embodiments, a compound of formula I is administered in a suitable dosage form prepared by combining a therapeutically effective amount of a compound of formula I with at least one excipient or carrier or diluent listed above according to conventional procedures well known in the art. The dosage form for treatment of cancer may be injected directly into tumors, injected into the blood stream or body cavities or taken orally or applied through the skin with patches.

The invention further provides kits comprising pharmaceutical compositions of an inventive compound. In certain embodiments, such kits include the combination of a compound of the present invention and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

EXEMPLIFICATION

Example 1

Preparation of naphtho[2,3-b]furan-4,9-dione (Compound XI)

To the solution of 5 grams (47.2 mmoles) of methyl vinyl sulfone in 100 mL of dichloromethane, 7.9 grams (49.5 mmoles) of bromine was added. The mixture was refluxed for 6 hours, and then evaporated to sticky residue. To the residue solution in 150 mL of tetrahydrofuran cooled in ice bath, 7.5 grams (49.5 mmoles) of 1,8-Diazabicyclo[5.4.0]undec-7-ene (DBU) was dropped slowly over 20 minutes while stirring vigorously. The reaction mixture was further stirred for 30 minutes in ice bath, then 8.2 grams (47.2 mmoles) of 2-hydroxy-1,4-naphthoquinone and 7.5 grams (49.5 mmoles) of 1,8-Diazabicyclo[5.4.0]undec-7-ene (DBU) were added. The mixture was reflux for 6 hours, and then evaporated to sticky residue. The residue was dissolved in 300 mL of dichloromethane, and washed with 300 mL of water, 300 mL of 2% aqueous citric acid solution, successively, and dried with 30 grams of anhydrous sodium sulfate. The naphtho[2,3-b]furan-4,9-dione product was purified with silica gel column using dichloromethane/hexane (3:1) as elution solvent. 2.3 grams of product (overall yield 25%) was obtained and characterized by $^1$H NMR and mass spectrum. $^1$H NMR (in DMSO) δ 7.17 (d, J=2, 1H), 7.86-7.91 (m, 2H), 8.09-8.13 (m, 2H), 8.32 (d, J=2.1H). Mass (M+H) is 199.

Example 2

Preparation of 2-acetyl-naphtho[2,3-b]furan-4,9-dione (Compound XIII, method 1)

Preparation of 3-buten-2-one

To an 1 L round-bottom flask, 600 ml of 4-hydroxy-2-butanone, 100 ml of water, 50 ml of methanol and 20 ml of 85% phosphoric acid were added. The mixture was stirred at room temperature for 30 minutes, and then distilled under reduced pressure (150-200 mmHg). Fraction at the boiling point of 65-80° C. was collected. To the collected fraction, 80 grams of sodium chloride was added. The resulting mixture was stirred at 4° C. for 1 hour, and then top organic layer was separated with funnel, dried with anhydrous sodium sulfate, and place at 4° C. for use.

Preparation of 2-acetyl-naphtho[2,3-b]dihydrofuran-4,9-dione

To a 500 ml round-bottom flask containing 16.1 grams (0.23 mol) of 3-buten-2-one and 40 ml of dichloromethane cooled in an ice-salt bath, 36.7 grams (0.23 mol) of bromine diluted in 10 ml of dichloromethane was added dropwise in 15 minutes. The mixture was washed with 50 ml of water, dried with anhydrous sodium sulfate, and evaporated to remove dichloromethane. 43.4 grams (0.19 mol) of the residue was transferred into an 1 L round-bottom flask, diluted with 40 ml of DMF and cooled in an ice-salt bath. While stirring vigorously, 27.3 grams (0.18 mol) of 1,8-Diazabicyclo[5.4.0]undec-7-ene (DBU) diluted with 50 ml of DMF was added dropwise in 15 minutes. To the mixture, 31.4 grams (0.18 mol) of 2-hydroxy-1,4-naphthoquinone was added, and the ice-salt bath was removed. While stirring vigorously and open in air, 25.8 grams (0.17 mol) of DBU diluted with 50 ml of DMF was added dropwise in 30 minutes at room temperature. After stirred for 4 hours, 500 ml of ice cooled water was added into the mixture. The crude product was filtered, washed with water, 5% aqueous sodium bicarbonate, water, 2% aqueous acetic acid solution, ice-cooled ethanol, successively. Pure product (21.8 grams, yield 50.1%) was obtained by crystallization in ethanol, and characterized by $^1$H NMR and mass spectrum. $^1$H NMR (in CDCl$_3$) δ 2.41 (s, 3H), 3.42-3.45 (m, 2H), 5.30 (m, 1H), 7.71-7.78 (m, 2H), 8.09-8.13 (m, 2H). Mass (M+H) is 243.

Preparation of 2-acetyl-naphtho[2,3-h]furan-4,9-dione

To a 500 ml round-bottom flask, 10 grams (41.3 mmoles) of 2-acetyl-naphtho[2,3-b]dihydrofuran-4,9-dione, 250 ml of ethanol and 5.1 grams (34 mmol) of DBU were added. While open in air, the mixture was refluxed for 30 minutes. After cooled in ice, 250 ml of ice water was added. The crude product was filtered, washed with water, 2% aqueous acetic acid solution, ice-cooled ethanol, successively. Pure product (7.93 grams, yield 80%) was obtained by crystallization in formic acid, and characterized by $^1$H NMR and mass spectrum. $^1$H NMR (in DMSO) δ 2.61 (s, 3H), 7.91-7.95 (m, 2H), 8.06 (s, 1H), 8.13-8.17 (m, 2H). Mass (M+H) is 241.

Example 3

Preparation of 2-acetyl-naphtho[2,3-h]furan-4,9-dione (Compound XIII, method 2)

To a 500 ml round-bottom flask containing 16.1 grams (0.23 mol, prepared as described in example 2) of 3-buten-2-one and 40 ml of dichloromethane cooled in an ice-salt bath, 36.7 grams (0.23 mol) of bromine diluted in 10 ml of dichloromethane was added dropwise in 15 minutes. The mixture was washed with 50 ml of water, dried with anhydrous sodium sulfate, and evaporated to remove dichloromethane. 43.4 grams (0.19 mol) of the residue was transferred into a 1 L round-bottom flask, diluted with 40 ml of DMF and cooled in an ice-salt bath. While stirring vigorously, 27.3 grams (0.18 mol) of 1,8-Diazabicyclo[5.4.0]undec-7-ene (DBU) diluted with 50 ml of DMF was added dropwise in 15 minutes. To the mixture, 31.4 grams (0.18 mol) of 2-hydroxy-1,4-naphthoquinone was added, and the ice-salt bath was removed. While stirring vigorously and open in air, 34.5 grams (0.23 mol) of DBU diluted with 50 ml of DMF was added dropwise in 30 minutes at room temperature. After stirred for 4 hours, 500 ml of ice cooled water was added to the mixture. The crude product was filtered, washed with water, 5% aqueous sodium bicarbonate, water, 2% aqueous acetic acid solution, ice-cooled ethanol, successively. Pure product (14.6 grams, yield 36.5%) was obtained by crystallization in formic acid, and characterized by $^1$H NMR and mass spectrum. $^1$H NMR (in DMSO) δ 2.61 (s, 3H), 7.91-7.95 (m, 2H), 8.06 (s, 1H), 8.13-8.17 (m, 2H). Mass (M+H) is 241.

Example 4

Preparation of 2-propionyl-naphtho[2,3-b]furan-4,9-dione (Compound XIV)

13.7 grams (54 mmoles) of 2-propionyl-naphtho[2,3-b]furan-4,9-dione was obtained from 16.0 grams (0.19 mol) of 1-penten-3-one and 31.4 grams (0.18 mol) of 2-hydroxy-1,4-naphthoquinone by using the procedure described in example 3 with overall yield 30.0%. $^1$H NMR (in DMSO) δ 1.12 (t, J=7, 3H), 3.05 (q, J=7, 2H), 7.92-7.94 (m, 2H), 8.03 (s, 1H), 8.13-8.17 (m, 2H). Mass (M+H) is 255.

Example 5

Preparation of 2-(1-hydroxyethyl)-naphtho[2,3-b]furan-4,9-dione (Compound XII)

In a 250 ml beaker, 2 grams (8.3 mmoles) of 2-acetyl-naphtho[2,3-b]furan-4,9-dione (prepared in example 2 or 3) was dissolved in 40 ml of DMF with heating. To the solution with stirring, 1 gram (26.4 mmoles) of sodium borohydride in 10 ml of water was added. The mixture was stirred in open air for 30 minutes, then diluted by adding 250 ml of water. The resulting mixture was extracted with 100 ml of dichloromethane twice. The combined organic phase was washed with 200 ml of water, dried with anhydrous sodium sulfate, and evaporated to dryness. The residue was crystallized in ethyl acetate to yield 1.6 gram (6.6 mmoles) of pure product with overall yield 80%. Pure product was characterized by $^1$H NMR and mass spectrum. $^1$H NMR (in DMSO) δ 1.47 (d, J=7, 3H), 4.88 (m, 1H), 5.83 (d, J=5, 1H), 6.91 (s, 1H), 7.84-7.90 (m, 2H), 8.06-8.11 (m, 2H). Mass (M+H) is 243.

Example 6

Preparation of 4,9-dimethoxy-naphtho[2,3-b]furan

To the solution of 2 grams (10.1 mmoles) of naphtho[2,3-b]furan-4,9-dione (prepared in example 1) in 150 mL of tetrahydrofuran/water (2:1), 7.03 grams (40.4 mmoles) of sodium hydrosulfite, 0.81 gram (20.2 mmoles) of sodium hydroxide, 0.64 gram (2 mmoles) of tetrabutylammonium bromide and 3.84 grams (40.4 mmoles) of methyl bromide were added at once. The mixture was stirred in a sealed round-bottom flask at room temperature for 4 hours, and then evaporated to remove tetrahydrofuran. The remaining aqueous solution was extracted with dichloromethane twice. The combined organic phase was washed with water, dried with anhydrous sodium sulfate, and evaporated to dryness. The product in the residue was purified with silica gel column using dichloromethane/hexane (2:1) as elution solvent. 1.8 grams of product (yield 80%) was obtained and characterized by $^1$H NMR and mass spectrum. $^1$H NMR (in CDCl$_3$) δ 4.20 (s, 3H), 4.30 (s, 3H), 7.06 (d, J=2, 1H), 7.45-7.53 (m, 2H), 7.67 (d, J=2, 1H), 8.26-8.32 (m, 2H). Mass (M+H) is 229.

Example 7

Preparation of 2-methylsulfonyl-naphtho[2,3-b]furan-4,9-dione (compound XV)

(1) Preparation of 2-trimethylsilyl-naphtho[2,3-b]furan-4,9-dione

To the solution of 4 mL 2.2 M n-butyl lithium diluted with 20 mL of anhydrous tetrahydrofuran in an ice bath, 1 gram (4.4 mmoles) of 4,9-dimethoxy-naphtho[2,3-b]furan (prepared in example 6) in 20 mL of anhydrous tetrahydrofuran was added dropwise over 5 minutes. The mixture was further stirred for 30 minutes in ice bath, and then 0.95 gram (8.8 mmoles) of chlorotrimethylsilane was added dropwise over 5 minutes. The mixture was stirred for additional 20 minutes in ice bath, and then further stirred for 30 minutes at room temperature. The reaction mixture was stopped by addition of 100 mL 0.1 N hydrochloric acid, and then evaporated to remove tetrahydrofuran. The remaining aqueous solution was extracted with dichloromethane twice. The combined organic phase was washed with water, dried with anhydrous sodium sulfate, and evaporated to dryness. The 1.2 gram (4 mmoles) of crude product 2-trimethylsilyl-4,9-dimethoxy-naphtho[2,3-b]furan was obtained, and was used for next step reaction without purification.

To 1.2 gram (4 mmoles) of crude product 2-trimethylsilyl-4,9-dimethoxy-naphtho[2,3-b]furan in 50 mL of acetonitrile/water (4:1) in ice bath, 4.8 grams (8.7 mmoles) of cerium ammonium nitrate (CAN) solution in 50 mL of acetonitrile/water (1:4) was added dropwise over 10 minutes. The mixture was further stirred in ice bath for 1 hour, and then evaporated to remove acetonitrile. The remaining aqueous suspension was filtered, and the collected solid was washed with water and crystallized in ethanol/water. Pure crystal product was filtered and dried under vacuum. 0.89 grams of product (overall yield 75%) was obtained and characterized by $^1$H NMR and mass spectrum. $^1$H NMR (in CDCl$_3$) δ 0.41 (s, 9H), 7.16 (s, 1H), 7.75-7.78 (m, 2H), 8.19-8.26 (m, 2H). Mass (M+H) is 271.

(2) Preparation of 2-bromo-naphtho[2,3-b]furan-4,9-dione

To the solution of 0.8 gram (3.0 mmoles) of 2-trimethylsilyl-naphtho[2,3-b]furan-4,9-dione in 20 mL of acetonitrile at room temperature, 0.53 grams (3.3 mmoles) of bromine in 20 mL of acetonitrile was added dropwise over 5 minutes. The mixture was further stirred for 30 minutes at room temperature, and then evaporated to dryness. The residue was crystallized in ethanol/water. Pure crystal product was filtered and dried under vacuum. 0.75 grams of product (yield 90%) was obtained and characterized by $^1$H NMR and mass spectrum. $^1$H NMR (in CDCl$_3$) δ 6.96 (s, 1H), 7.76-7.82 (m, 2H), 8.18-8.25 (m, 2H). Mass (M+H) is 277 and 279.

(3) Preparation of 2-methylthio-naphtho[2,3-b]furan-4,9-dione

To the solution of 0.7 gram (2.5 mmoles) of 2-bromo-naphtho[2,3-b]furan-4,9-dione in 20 mL of tetrahydrofuran at room temperature, 0.4 grams (5.0 mmoles) of MeSNa in 5 mL of water was added dropwise over 1 minute. The mixture was further stirred for 2 hours at room temperature, and then evaporated to remove tetrahydrofuran. To the residue, 20 mL of 1 N hydrochloric acid was added, and the resulting mixture was filtered. The solid was washed with water, and then crystallized in ethanol/water. Pure crystal product was filtered and dried under vacuum. 0.55 grams of product (yield 90%) was obtained and characterized by $^1$H NMR and mass spectrum. $^1$H NMR (in CDCl$_3$) δ 2.66 (s, 3H), 6.79 (s, 1H), 7.75-7.79 (m, 2H), 8.18-8.25 (m, 2H). Mass (M+H) is 245.

(4) Preparation of 2-methylsulfonyl-naphtho[2,3-b]furan-4,9-dione (compound XV)

To a solution of 0.5 gram (2.05 mmoles) of 2-methylthio-naphtho[2,3-b]furan-4,9-dione in 30 mL of dichloromethane in ice bath, 0.57 grams (2.46 mmoles) of 70% purity 3-chloroperbenzoic acid was added. The mixture was stirred in ice bath for 30 minutes, further stirred for 2 hours at room temperature, then diluted with 100 mL of dichloromethane and washed with 150 mL of 5% sodium bicarbonate twice. The organic phase was dried with anhydrous sodium sulfate, and evaporated to dryness. The residue was crystallized in ethanol/water. 0.48 grams of product (yield 85%) was obtained and characterized by $^1$H NMR and mass spectrum. $^1$H NMR (in CDCl$_3$) δ 3.34 (s, 1H), 7.68 (s, 1H), 7.85-7.87 (m, 2H), 8.26-8.30 (m, 2H). Mass (M+H) is 277.

Example 8

Preparation of 2-methylsulfinyl-naphtho[2,3-b]furan-4,9-dione (compound XVI)

To a solution of 0.5 gram (2.05 mmoles) of 2-methylthio-naphtho[2,3-b]furan-4,9-dione (prepared in example 7) in 20 mL of acetonitrile at room temperature, 0.49 grams (2.15 mmoles) of periodic acid followed by 2 mg of ferric chloride was added. The mixture was stirred for 10 minutes at room temperature, then 50 mL of water was added, and the resulting mixture was evaporated to remove acetonitrile. The remaining aqueous suspension was filtered, and the obtained solid was washed with water and dried under vacuum. The crude solid product was purified with silica gel chromatograph using dichloromethane/ethyl acetate (9:1) as elution solvent. 0.43 grams of product (yield 80%) was obtained and characterized by $^1$H NMR and mass spectrum. $^1$H NMR (in DMSO) δ 3.14 (s, 3H), 7.81 (s, 1H), 7.92-7.94 (m, 2H), 8.12-8.17 (m, 2H). Mass (M+H) is 261.

Example 9

Preparation of 2-acetyl-4,9-bis(acetoxy)-naphtho[2,3-b]furan

In a 500 ml round-bottom flask, 8 grams (33.3 mmoles) of 2-acetyl-naphtho[2,3-b]furan-4,9-dione (prepared in example 2 or 3) was dissolved in 150 ml of DMF with heating. To the solution, added 14 ml of TEA, 8 grams of zinc powder, 1 gram of tetrabutylammonium bromide and 29 grams (166.7 mmoles) of sodium hydrosulfite. The mixture was sealed or isolated from air. Then 17 grams (166.7 mmoles) of acetic anhydride was added with syringe, and the resulting mixture had been stirred vigorously at room temperature for 3 hours. After addition of 300 ml of ethyl acetate, the reaction mixture was filtered, and the solid was washed with 200 ml of ethyl acetate. The filtrates were combined, extracted with 300 ml of ice-cooled aqueous 3% citric acid solution twice, and dried with anhydrous sodium sulfate. The organic phase was evaporated to dryness. The residue was washed with 60 ml of ice-cooled ethanol, and then filtered solid was crystallized in 250 ml of ethanol. 5.5 grams (16.9 mmoles, yield 50.7%) of product was obtained and characterized by $^1$H NMR and mass spectrum. $^1$H NMR (in CDCl$_3$) δ 2.59 (s, 3H), 2.62 (s, 3H), 2.66 (s, 3H), 7.50 (s, 1H), 7.53-7.62 (m, 2H), 8.00-8.03 (m, 2H). Mass (M+H) is 327, Mass (M+Na) is 349.

Example 10

Preparation of 2-acetyl-4,9-Bis(isobutoxy)-naphtho[2,3-b]furan (compound I)

9.41 grams (24.6 mmoles) of product was obtained from 8 grams (33.3 mmoles) of 2-acetyl-naphtho[2,3-b]furan-4,9-dione (prepared in example 2 or 3) and 26.4 grams (166.7 mmoles) of isobutyric anhydride instead of acetic anhydride by using the procedure described in example 9 with overall yield of 74.0%. Product was characterized by $^1$H NMR and mass spectrum. $^1$H NMR (in CDCl$_3$) δ 1.54 (d, J=7, 6H), 1.56 (d, J=7, 6H), 2.65 (s, 3H), 3.11-3.20 (m, 2H), 7.43 (s, 1H), 7.53-7.60 (m, 2H), 7.99-8.02 (m, 2H). Mass (M+H) is 383.

Example 11

Preparation of 2-acetyl-4,9-Bis(pivaloxy)-naphtho[2,3-b]furan (compound II)

8.37 grams (20.4 mmoles) of product was obtained from 8 grams (33.3 mmoles) of 2-acetyl-naphtho[2,3-b]furan-4,9-dione (prepared in example 2 or 3) and 20.1 grams (166.7 mmoles) of pivaloyl chloride instead of acetic anhydride by using the procedure described in example 9 with overall yield of 61.3%. Product was characterized by $^1$H NMR and mass spectrum. $^1$H NMR (in CDCl$_3$) δ 1.59 (s, 9H), 1.61 (s, 9H), 2.65 (s, 3H), 7.40 (s, 1H), 7.51-7.61 (m, 2H), 7.97-8.00 (m, 2H). Mass (M+H) is 411.

Example 12

Preparation of 2-acetyl-4-hydroxy-9-[(tert-butoxycarbonyl)amino]acetoxy-naphtho[2,3-b]furan (compound III)

In a 250 ml round-bottom flask, 2 grams (8.3 mmoles) of 2-acetyl-naphtho[2,3-b]furan-4,9-dione (prepared in example 2 or 3) was dissolved in 50 ml of DMF with heating. To the solution, added 3.5 ml of TEA, 2 grams of zinc powder, 0.3 gram of tetrabutylammonium bromide, 2.33 grams (13.3 mmoles) of [(tert-butoxycarbonyl)amino]acetic acid, 5.04 grams (13.3 mmoles) of N,N,N',N'-Tetramethyl-O-(1H-benzotriazol-1-yl)uronium hexafluorophosphate (HBTU) and 7.25 grams (41.7 mmoles) of sodium hydrosulfite. The mixture was sealed or isolated from air, and then had been stirred vigorously at room temperature overnight. After addition of 100 ml of ethyl acetate, the reaction mixture was filtered, and the solid was washed with 50 ml of ethyl acetate. The filtrates were combined, extracted with 100 ml of ice-cooled aqueous 3% citric acid solution twice, and dried with anhydrous sodium sulfate. The organic phase was evaporated to dryness. Product was purified by silica gel chromatograph using dichloromethane/ethyl acetate (4:1) as elution solvent. 1.64 gram (4.1 mmoles) of product was obtained with yield of 49.4% and characterized by $^1$H NMR and mass spectrum. $^1$H NMR (in DMSO) δ 1.44 (s, 9H), 2.59 (s, 3H), 4.28 (d, J=6, 2H), 7.49-7.65 (m, 3H), 7.97 (m, 1H), 8.20-8.35 (m, 2H), 11.4 (s, 1H). Mass (M+H) is 400, Mass [M-(tert-butyl)+2H] is 344.

Example 13

Preparation of 2-acetyl-4-acetoxy-9-[(tert-butoxycarbonyl)amino]acetoxy-naphtho[2,3-b]furan (compound IV)

In an 100 ml round-bottom flask, 0.8 gram (2.0 mmoles) of 2-acetyl-4-hydroxy-9-[(tert-butoxycarbonyl)amino]acetoxy-naphtho[2,3-b]furan (prepared in example 12) was dissolved in 30 ml of DMF with mild heating. To the solution, added 0.9 ml of TEA and 0.5 ml of acetic anhydride. The mixture was sealed or isolated from air, and then had been stirred vigorously at room temperature overnight. After addition of 100 ml of ethyl acetate, the reaction mixture was extracted with 80 ml of ice-cooled aqueous 3% citric acid solution twice, and dried with anhydrous sodium sulfate. The organic phase was evaporated to dryness. Product was purified by silica gel chromatograph using dichloromethane as elution solvent. 0.6 gram (1.36 mmole) of product was obtained with yield of 68.0% and characterized by $^1$H NMR and mass spectrum. $^1$H NMR (in DMSO) δ 1.44 (s, 9H), 2.62 (s, 3H), 2.63 (s, 3H), 4.34 (d, J=6, 2H), 7.67-7.71 (m, 3H), 8.15-8.17 (m, 2H), 8.25 (s, 1H). Mass (M+H) is 442, Mass [M-(tert-butyl)+2H] is 386.

Example 14

Preparation of 2-propionyl-4,9-Bis{[(tert-butoxycarbonyl)amino]acetoxy}-naphtho[2,3-b]furan (compound V)

In a 250 ml round-bottom flask, 2 grams (7.87 mmoles) of 2-propionyl-naphtho[2,3-b]furan-4,9-dione (prepared in example 4) was dissolved in 50 ml of DMF with heating. To the solution, added 3.5 ml of TEA, 2 grams of zinc powder, 0.3 gram of tetrabutylammonium bromide, 4.14 grams (23.61 mmoles) of [(tert-butoxycarbonyl)amino]acetic acid, 8.95 grams (23.61 mmoles) of N,N,N',N'-Tetramethyl-O-(1H-benzotriazol-1-yl)uronium hexafluorophosphate (HBTU) and 7.25 grams (41.7 mmoles) of sodium hydrosulfite. The mixture was sealed or isolated from air, and then had been stirred vigorously at room temperature overnight. After addition of 100 ml of ethyl acetate, the reaction mixture was filtered, and the solid was washed with 50 ml of ethyl acetate. The filtrates were combined, extracted with 100 ml of ice-cooled aqueous 3% citric acid solution twice, and dried with anhydrous sodium sulfate. The organic phase was evaporated to dryness. Product was purified by silica gel chromatograph using dichloromethane/ethyl acetate (10:1) as elution solvent. 1.83 gram (3.21 mmoles) of product was obtained with yield of 40.8% and characterized by $^1$H NMR and mass spectrum. $^1$H NMR (in DMSO) δ 1.15 (t, J=7, 3H), 1.44 (s, 9H), 1.46 (s, 9H), 3.06 (q, J=7, 2H), 4.31-4.35 (m, 4H), 7.62-7.77 (m, 4H), 8.11-8.20 (m, 3H). Mass (M+H) is 571, Mass [M-(tert-butyl)+2H] is 515, Mass [M-2(tert-butyl)+3H] is 459.

Example 15

Preparation of 2-acetyl-4,9-Bis(dichloroacetoxy)-naphtho[2,3-b]furan (compound VI)

4.0 grams (8.6 mmoles) of product was obtained from 8 grams (33.3 mmoles) of 2-acetyl-naphtho[2,3-b]furan-4,9-dione (prepared in example 2 or 3), 40.1 grams (166.7 mmoles) of dichloroacetic anhydride instead of acetic anhydride and 2 grams instead of 8 grams of zinc with overall yield of 25.8% by using the procedure described in Example 9. Product was characterized by $^1$H NMR and mass spectrum. $^1$H NMR (in CDCl$_3$) δ 2.68 (s, 3H), 6.43 (s, 1H), 6.50 (s, 1H), 7.51 (s, 1H), 7.62-7.72 (m, 2H), 8.11-8.15 (m, 2H). Mass (M+H) is 463, 465, 467; Mass (M+Na) is 485, 487, 489.

Example 16

Preparation of amorphous solid of 2-acetyl-naphtho[2,3-b]furan-4,9-dione (compound XIII)

Figure 8:
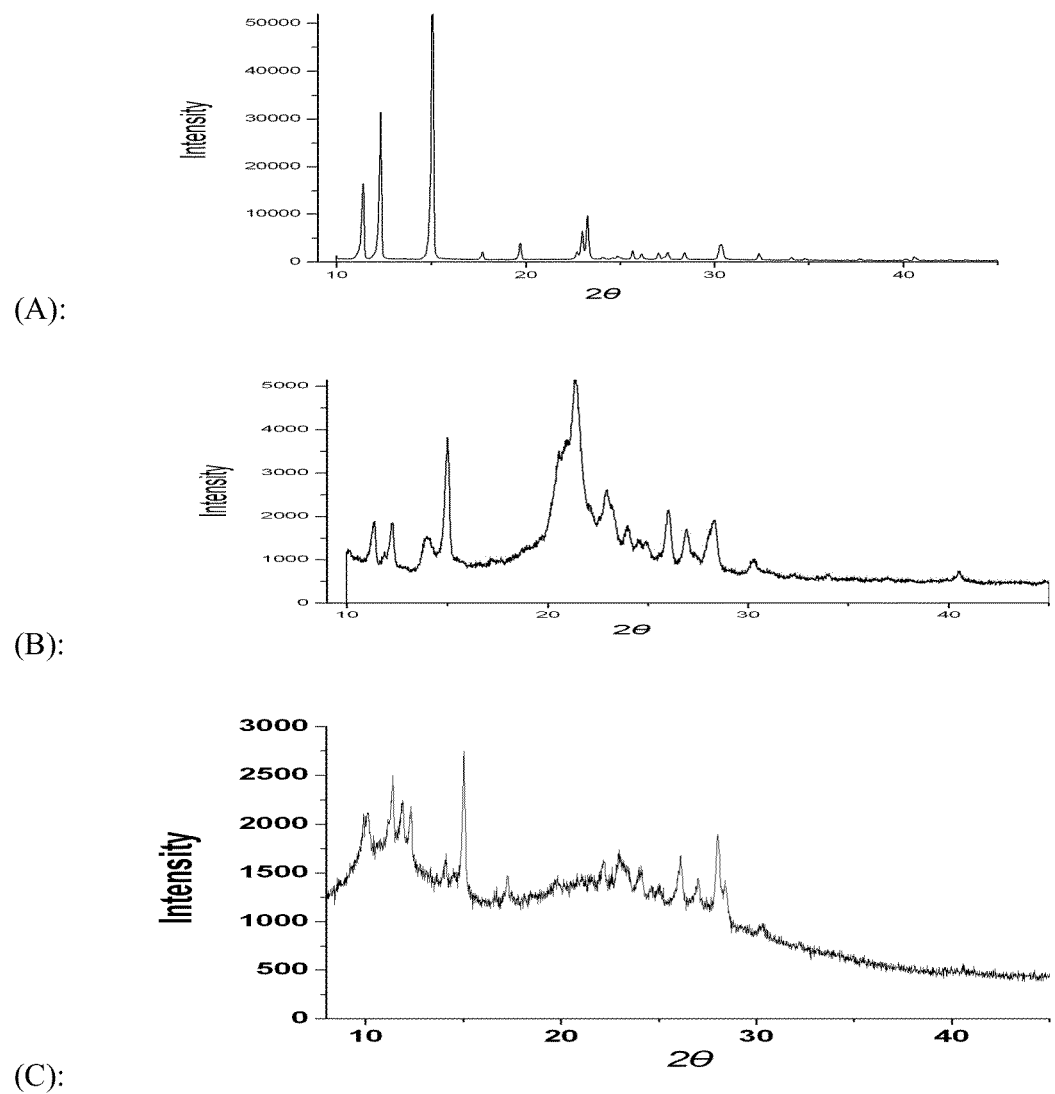
FIG. 8. X-ray powder diffractions. (A) crystalline of compound XIII; (B) amorphous mixture of 1,2-dimyristoyl-sn-glycerophosphocholine (DMPC) and compound XIII (2:1); (C) amorphous mixture of Plasdone K-25 (PVP) and compound XIII (2:1); (D) crystalline of 2-acetyl-4,9-bis(acetoxy)-naphtho[2,3-b]furan; (E) amorphous mixture of DMPC and 2-acetyl-4,9-bis(acetoxy)-naphtho[2,3-b]furan (2:1); (F) amorphous mixture of PVP and 2-acetyl-4,9-bis (acetoxy)-naphtho[2,3-b]furan (1:1).
Figure 8:
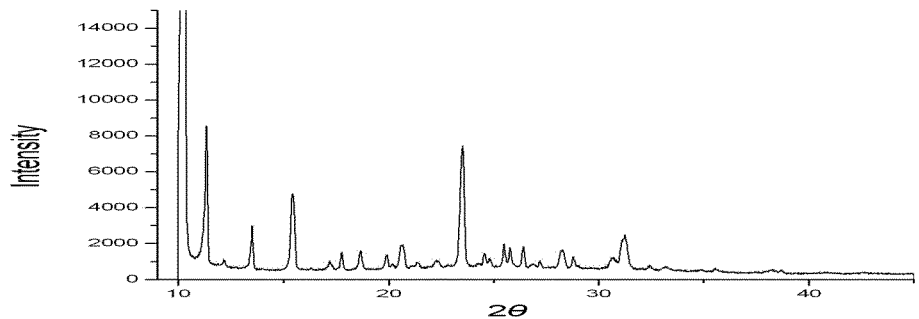
Figure 8:
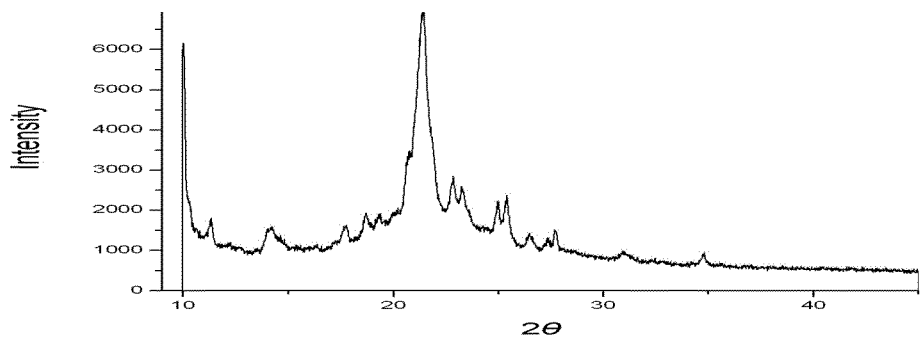
Figure 8:
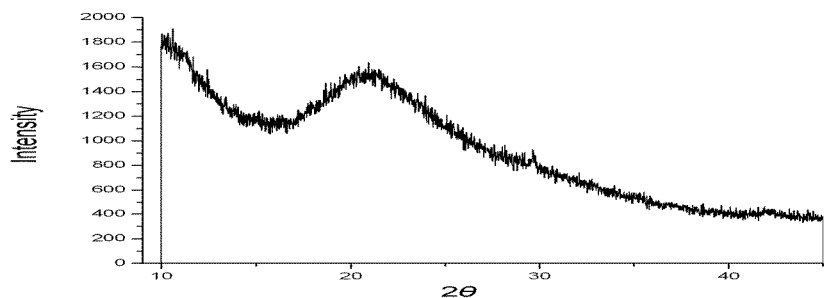

Mixture of 5.0 grams of 2-acetyl-naphtho[2,3-b]furan-4,9-dione and 10 grams of Plasdone K-25 or 10 grams of 1,2 dimyristoyl-sn-glycerophosphocholine (DMPC) was dissolved in 2,000 nil of dichloromethane. The mixture solution was then spray-dried with Labplant, SD-Basic mini spray dryer with inlet temperature at 90° C. and outlet temperature at 45° C. The dried powder is subject to XRD crystalline morphological analysis (FIG. 8).

Example 17

Preparation of amorphous solid of 2-acetyl-4,9-diacetoxy-naphtho[2,3-b]furan or a compound of formula I Mixture of 5.0 grams of 2-acetyl-4,9-diacetoxy-naphtho[2,3-b]furan or a compound of formular 1 and 10 grams of Plasdone K-25 or 10 grams of 1,2 dimyristoyl-sn-glycerophosphocholine (DMPC) was dissolved in 500 ml of acetone. The mixture solution was then Rot-yap dried quickly under vacuum and high water bath temperature (45-50° C.). The dried powder is subject to XRD crystalline morphological analysis (FIG. 8).

Example 18

Studies Involving HPLC Analysis

HPLC column: Waters Sunfire C18, 250×4.60 mm 5 micron; Mobile phase: buffer A, 90% 5 mM potassium phosphate buffer, pH 6.8, 10% acetonitrile; buffer B, 15% 5 mM potassium phosphate buffer, pH 6.8, 85% acetonitrile; Detector: Waters 2998 Photodiode Array Detector.

Gradient A: 0-3 min, 20% buffer B, 3-23 min, 20%-100% buffer B, 23-26 min, 100% buffer B, 26-28 min, 100%-20% buffer B, 28-30 min, 20% buffer B; flow rate, 1 ml/min.

Gradient B: 0-3 min, 50% buffer B, 3-5 min, 50%-100% buffer B, 5-18 min, 100% buffer B, 18-22 min, 100%-50% buffer B, 22-25 min, 20% buffer B; flow rate, 1 ml/min. Analysis of the 4,9-dihydroxy-naphtho[2,3-b]furan compounds (FIG. 1)

To 1 ml of 50 mM sodium hydrosulfite and 1 mM sodium hydroxide aqueous solution, 10 μl of 10 mM naphtho[2,3-b]furan-4,9-dione compound was added and vortexed in a sealed vial for 5 minutes. 10 μl of the mixture was used for HPLC analysis using gradient A.
Analysis of the Compounds of Formula I and their Human Plasma Incubation Mixtures (FIG. 2)

10 mM of a compound of formula I in DMSO (however, compound VI was in DMF) was diluted with 50% acetonitrile to 10 μM and 10 μl of the mixture was used for HPLC analysis using gradient B.

10 mM of a compound of formula I or its analog in DMSO (however, compound VI was in DMF) was diluted with human plasma to 20 μM, and the resulting mixtures were incubated at 37° C. for 2 hours. To plasma sample, 9 times volume of acetonitrile was added. The resulting mixtures were vortexed and incubated in dry ice for 30 minutes or in −20° C. freezer for 3 hours, then centrifuged, and supernatant was used for HPLC analysis using gradient B.
Analysis of Whole Blood Samples (FIGS. 3 and 9) or Other Biological System Samples
Preliminary Study of In Vivo Metabolism and Oral Uptake of a Compound of Formula I or its Analog or Compound XIII Crystalline or amorphous solid of compound was mixed with excipient and suspended in 0.5% carboxymethylcellulose (CMC) solution in a mortar. Then the mixture was orally administered into ICR mouse at the predetermined dosage. At the predetermined time point, blood was drawn from the mouse and stored in the vial containing heparin. The blood samples were centrifuged at 6,000 rpm for 10 min, and plasmas were separated. To each plasma sample, 9 times volume of acetonitrile/methyl trifluoromethanesulfonate (1000:1) or acetonitrile/concentrated HCl (1000:1) was added. The resulting mixtures were vortexed and incubated in dry ice for 30 minutes or in −20° C. freezer for 3 hours, then centrifuged, and supernatants were separated for HPLC analysis using gradient B.
Preliminary Study of In Vitro Metabolism of a Compound of Formula I or its Analog or Compound XIII The biological systems for in vitro metabolism study include: human whole blood stabilized with sodium citrate; cancer cell lysate (obtained using freeze-thaw method, 10 mg/ml in protein concentration for use); liver microsomes with NADPH generation system (prepared according to the protocol provided by iPhase Pharma, Beijing, China);

10 mM of a compound of formula I or its analog or compound XIII in DMSO (however, compound VI was in DMF) was added into the biological system to a final concentration of 20 μM. The mixtures were incubated at 37° C. for predetermined time. To each sample, then 9 times volume of acetonitrile was added. The resulting mixtures were vortexed and incubated in dry ice for 30 minutes or in −20° C. freezer for 3 hours, then centrifuged, and supernatants were separated for HPLC analysis using gradient B.

Example 19

Biological Assays

Cell Culture: A549, DLD1, SW480, LOVO, HT-29, Hela, U-20S, MES-SA, SK-MEL-28, Panc-1, DU-145, CNE, U251, Eca-109, MGC80-3, QGY-7701, BEL-7404, PLC/PRF/5, Huh-7, and SGC-7901 cells were maintained in Dulbecco's Modified Eagle Medium (DMEM) (imported from Invitrogen, Carlsbad, Calif., USA) supplemented with 10% fetal bovine serum (FBS) (Si Ji Qing, Hangzhou, China) and 1% penicillin/streptomycin/amphotericin B (imported from Invitrogen, Carlsbad, Calif., USA).

Cell Viability Determination: Popular MTT method (*Archives of Biochemistry and Biophysics*, 1993, 303: 474-482) was used to screen the in vitro effects of the invented drugs. Briefly, 5000 to 10000 cells were inoculated per well in a 96-well plate. After overnight incubation, drug was added to the wells at final concentration of 10 μM, 50 μM, 2.5 μM, 1.25 μM, or 1 μM, 0.75 μM, 0.5 μM and 0.25 μM in complete culture medium. Each dose level covered 4 equivalent wells. After 48 hour incubation, one tenth volume of 5 mg/mL MTT (thiazolyl blue tetrazolium bromide, Sigma-Aldrich) stock solution was added, and incubation was continued for 2 hours. Then medium was removed and 100 μL of isopropanol solution comprising 86% isopropanol, 4% aqueous 1 N HCl and 10% aqueous SDS solution (10% in concentration) was added. The absorbance of each well at 570 nm wavelength was measured by a micro-plate reader after gentle shaking for 20 minutes. Drug concentrations of 50% cell viability (IC50) were calculated by LOGIT method.

TABLE 3

| | | Drug concentrations for 50% cell viability (IC50, μM). | | | | | |
|---|---|---|---|---|---|---|---|
| Type of Cancer | Name of Cell line | 2-acetyl-4,9-bis(acetoxy)-naphtho[2,3-b]furan | The Compounds of Formula I | | | | |
| | | | I | II | III | IV | VI |
| lung cancer | A549 | 1.70 | <2.50 | n/a | 1.25-2.5 | 0.60 | 0.40 |
| colorectal cancer | DLD1 | 1.80 | <2.50 | >4 | 1.03 | 0.30 | 0.90 |
| | SW480 | 0.86 | <2.50 | >4 | 1.55 | 0.91 | 0.60 |

TABLE 3-continued

Drug concentrations for 50% cell viability (IC50, µM).

| Type of Cancer | Name of Cell line | 2-acetyl-4,9-bis(acetoxy)-naphtho[2,3-b]furan | The Compounds of Formula I | | | | |
|---|---|---|---|---|---|---|---|
| | | | I | II | III | IV | VI |
| | LOVO | 1.10 | 2.80 | >4 | 3.10 | 1.93 | 1.50 |
| cervical cancer | Hela | 1.20 | <2.50 | n/a | 1.25-2.50 | 0.86 | 0.40 |
| osteosarcoma | U-20S | 1.00 | 5.70 | n/a | 2.5-5 | 0.75-1.00 | 0.80 |
| leiomyosarcoma | MES-SA | 0.60 | <2.50 | n/a | 0.47 | 0.42 | 0.27 |
| malignant melanoma | SK-MEL-28 | 0.30 | n/a | n/a | 0.89 | 0.25-0.50 | n/a |
| pancreatic cancer | Panc-1 | 1.50 | <2.5 | 3.00 | 1.77 | 0.87 | 1.00 |
| prostate cancer | DU-145 | 1.00 | <2.5 | n/a | 1.25-2.50 | 0.25-0.5 | 1.00 |
| nasopharyngeal cancer | CNE | 1.50 | 2.50 | n/a | 1.87 | 1.33 | 1.10 |
| glioma | U251 | 1.08 | <2.5 | n/a | 2.07 | 1.14 | 0.70 |
| esophageal cancer | Eca-109 | 1.40 | 5.50 | >4 | 2.55 | 1.63 | 0.80 |
| stomach cancer | MGC80-3 | n/a | 2.50 | n/a | 1.65 | 1.22 | 0.60 |
| liver cancer | QGY-7701 | n/a | 2.87 | n/a | 4.80 | 3.26 | n/a |

[1] n/a = Not tested.

Determination of NQ01 Enzymatic Activity in Cell Lysate (Part A of FIG. 4): Assay was performed as described in the paper (Traver R D, et al. *British Journal of Cancer*, 1997, 75: 69-75). Cancer cells were grown to 80% confluence, and then washed with PBS buffer and scraped into ice-cold buffer (25 mM Tris-HCl, pH7.4, 125 mM sucrose). The cancer cell suspension had been frozen-thawed for three times and then adjusted to 5 mg/ml in protein concentration. The mixture was used as cell lysate for NQ01 enzymatic activity assay. Assay mixture comprised 25 mM Tris-HCl, pH7.4, 0.7 mg/ml bovine serum albumin (BSA), 0.2 mM NADH and 40 µM dichlorophenolindophenol (DCPIP); Dicumarol (NQ01 inhibitor) was added to the assay mixture as reference solution. 1% volume of cell lysate was added into the assay mixture and the reference solution, respectively. The resulting mixtures were incubated at 25° C. for 10 minutes. The relative NQ01 enzymatic activity was obtained by the absorbance difference at 600 nm between the incubated assay mixture and the reference solution.

Effect of NQ01 Inhibitor (Dicumarol) on the Biological Activities of 2-acetyl-4,9-diacetoxy-naphtho[2,3-b]furan and Compound XIII (Part B and C of FIG. 4):MTT assay was used for this experiment. Same procedure as described in "Cell Viability Determination" section. Briefly, cancer cells were inoculated on 96 well culture plates. After overnight incubation, drug was added into each well at the final concentration as indicated in FIG. 4. Another set of wells were added with the same drug plus dicumarol at the final concentration of 40 µM. The viability of cells at each well was read out after 48 hr incubation in cell culture incubator.

Evaluation of Reactive Oxygen Species (ROS) Level in Cells with Fluorescence Microscope (FIG. 5):To each well on an 8 well plate, filled 1,000 µl of DLD1 cell suspension (100-150 cells/0 in culture medium, then incubated the plate at 37° C. overnight. The seeded cells in the plate were washed with PBS buffer twice, and then added freshly prepared 40 µM dichlorofluorescin diacetate (DCFH-DA) in culture medium, and incubated the mixture for 5 min at 37° C. Following several PBS washes, cells were exposed to 1,000 µl medium containing: 0.3 µM test compound, or 100 µM hydrogen peroxide, or DMSO only (control). After incubation for 30 min at 37° C., the fluorescence picture was taken from each well by using a fluorescence microscope (Olympus IX70 Inverted) with the excitation filter set at 488 nm and the emission filter at 530 nm.

Effect of Antioxidant N-acetyl-L-cysteine (NAC) on the Biological Activities of Hydrogen Peroxide and Compound XIII (FIG. 6): MTT assay was used for this experiment. Same procedure as described in "Cell Viability Determination" section. Briefly, cancer cells were inoculated on 96 well culture plates. After overnight incubation, hydrogen peroxide (or drug) was added into each well at the final concentration as indicated in FIG. 6. Another set of wells were added with NAC to concentration of 40 mM first, 30 minutes later added with the same hydrogen peroxide (or drug). The viability of cells at each well was read out after 48 hr incubation in cell culture incubator.

Effect of Drug Incubation Time on the Biological Activities of Compound XIII (FIG. 7): MTT assay was used for this experiment. Same procedure as described in "Cell Viability Determination" section. Briefly, cancer cells were inoculated on 96 well culture plates. After overnight incubation, compound XIII was added into each well at the final concentration as indicated in FIG. 7. After 4 hours incubation, the 4 hour treatment plates were washed by culture medium to remove drug and refilled with fresh medium, then all plates were incubated for additional 48 hours. The viability of cells at each well was read out using MTT method.

Preliminary Toxicity Study of Compound I and XIII (FIGS. 8 and 10): Amorphous solid of compound I or XIII was suspended in 0.5% carboxymethylcellulose (CMC) solution in a mortar at concentration of 90 mg/ml for compound I and 60 mg/ml for compound XIII. Then each of the mixtures was then orally administered into three ICR mice (30 grams in average weight) with gavage feeding at the dosage of 1,200 mg/kg for compound I or 800 mg/ml for compound XIII once daily for 7 days. Weight of each mouse was recorded before gavage feeding.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

Incorporation of References

All publications and patent documents cited in this application are incorporated by reference in their entirety to the same extent as if the contents of each individual publication or patent document were incorporated herein.

What is claimed is:

1. A compound of formula I:

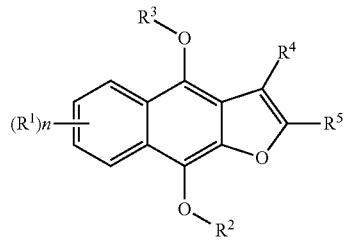

I or a pharmaceutically acceptable salt thereof;
wherein:
n is 0-4;
each $R^1$ is independently halogen; —$NO_2$; —CN; —OR; —SR; —$N^+(R)_3$; —$N(R)_2$; —C(O)R; —$CO_2R$; —C(O)C(O)R; —C(O)$CH_2$C(O)R; —S(O)R; —S(O)$_2$R; —C(O)N(R)$_2$; —$SO_2$N(R)$_2$; —OC(O)R; —N(R)C(O)R; —N(R)N(R)$_2$; —N(R)C(=NR)N(R)$_2$; —C(=NR)N(R)$_2$; —C=NOR; —N(R)C(O)N(R)$_2$; —N(R)$SO_2$N(R)$_2$; —N(R)$SO_2$R; —OC(O)N(R)$_2$; or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl, or:
two $R^1$ groups on adjacent carbon atoms are taken together with their intervening atoms to form an optionally substituted ring selected from 3- to 14-membered carbocycle; 3- to 14-membered heterocycle; a 6- to 14-membered aryl ring; or a 5- to 14-membered heteroaryl ring;
each $R^2$ and $R^3$ is independently hydrogen, —S(=O)$_2$OR$^a$, —P(=O)OR$^a$OR$^b$, or —C(=O)R$^c$; wherein each $R^a$ and $R^b$ is independently hydrogen, sodium, potassium, an amine cation, or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl; or:
$R^a$ and $R^b$ are taken together with their intervening atoms to form an optionally substituted 3- to 14-membered heterocycle;
$R^c$ is hydrogen, —N(R)$_2$; —OR; —SR; or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl;
$R^4$ is hydrogen; halogen; —$NO_2$; —OR; —SR; —$N^+(R)_3$; —$N(R)_2$; —C(O)R; —$CO_2R$; —C(O)C(O)R; —C(O)$CH_2$C(O)R; —S(O)R; —S(O)$_2$R; —C(O)N(R)$_2$; —$SO_2$N(R)$_2$; —OC(O)R; —N(R)C(O)R; —N(R)N(R)$_2$; —N(R)C(=NR)N(R)$_2$; —C(=NR)N(R)$_2$; —C=NOR; —N(R)C(O)N(R)$_2$; —N(R)$SO_2$N(R)$_2$; —N(R)$SO_2$R; —OC(O)N(R)$_2$; or an optionally substituted group selected from $C_{1-12}$ aliphatic; 3- to 14-membered carbocyclyl; 3- to 14-membered heterocyclyl; 6- to 14-membered aryl; or 5- to 14-membered heteroaryl;

$R^5$ is halogen; —$NO_2$; —CN; —OR; —SR; —$N^+(R)_3$; —$N(R)_2$; —C(O)R; —$CO_2R$; —C(O)C(O)R; —C(O)$CH_2$C(O)R; —S(O)R; —S(O)$_2$R; —C(O)N(R)$_2$; —$SO_2$N(R)$_2$; —OC(O)R; —N(R)C(O)R; —N(R)N(R)$_2$; —N(R)C(=NR)N(R)$_2$; —C(=NR)N(R)$_2$; —C=NOR; —N(R)C(O)N(R)$_2$; —N(R)$SO_2$N(R)$_2$; —N(R)$SO_2$R; —OC(O)N(R)$_2$; or an optionally substituted group selected from $C_{1-12}$ aliphatic; 3- to 14-membered carbocyclyl; 3- to 14-membered heterocyclyl; or 5- to 14-membered heteroaryl; provided that $R^5$ is not methyl or ethyl;
each R is independently hydrogen or an optionally substituted group selected from $C_{1-12}$ aliphatic; a 3- to 14-membered carbocycle; a 3- to 14-membered heterocycle; a 6- to 14-membered aryl ring; or a 5- to 14-membered heteroaryl ring;
provided that:
(a) when $R^2$ and $R^3$ are each acetyl, then $R^1$ is not acetoxy;
(b) when $R^2$ and $R^3$ are each acetyl and $R^4$ is ethoxycarbonyl, then $R^5$ is not 2-oxo-propyl; and
(c) when $R^2$, $R^3$ and $R^5$ are each acetyl, then either $R^1$ or $R^4$ is not hydrogen.

2. The compound of claim 1, wherein n is 0.
3. The compound of claim 1, wherein n is 1.
4. The compound of claim 1, wherein $R^1$ is halogen.
5. The compound of claim 1, wherein $R^2$ is hydrogen.
6. The compound of claim 1, wherein $R^2$ is -C(=O)$R^c$, wherein $R^c$ is optionally substituted $C_{1-12}$ aliphatic.
7. The compound of claim 1, wherein $R^2$ is —P(=O)OR$^a$OR$^b$, wherein $R^a$ and $R^b$ are each independently hydrogen, sodium, or potassium.
8. The compound of claim 1, wherein $R^2$ is —S(=O)$_2$OR$^a$, wherein $R^a$ is selected from hydrogen, sodium, or potassium.
9. The compound of claim 1, wherein $R^3$ is hydrogen.
10. The compound of claim 1, wherein $R^3$ is -C(=O)$R^c$, wherein $R^c$ is optionally substituted $C_{1-12}$ aliphatic.
11. The compound of claim 1, wherein $R^3$ is —P(=O)OR$^a$OR$^b$, wherein $R^a$ and $R^b$ are each independently hydrogen, sodium, or potassium.
12. The compound of claim 1, wherein $R^3$ is —S(=O)$_2$OR$^a$, wherein $R^a$ is selected from hydrogen, sodium, or potassium.
13. The compound of claim 1, wherein $R^4$ is hydrogen.
14. The compound of claim 1, wherein $R^5$ is —C(O)R, wherein R is optionally substituted $C_{1-12}$ aliphatic.
15. The compound of claim 1, wherein $R^5$ is —C(O)R, wherein R is optionally substituted 6- to 14-membered aryl.
16. The compound of claim 14, wherein R is methyl.
17. The compound of claim 1, selected from the group consisting of:

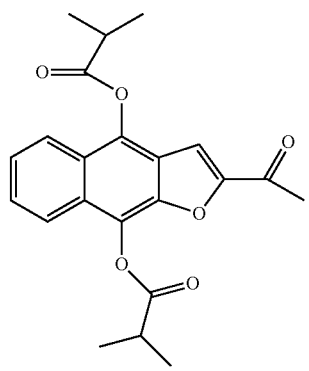

compound I

-continued
compound II
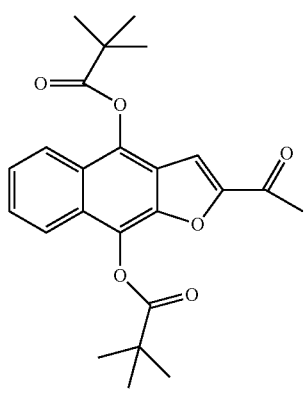
compound III
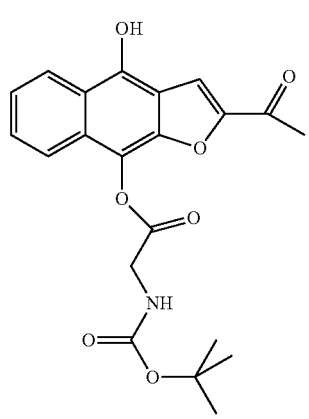
compound IV
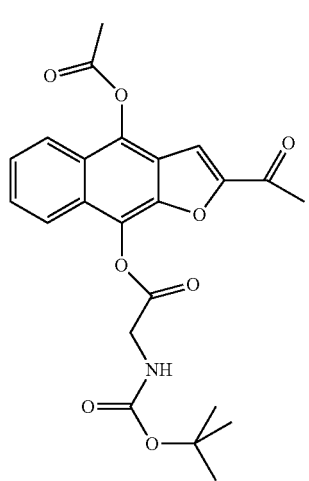
-continued
compound V
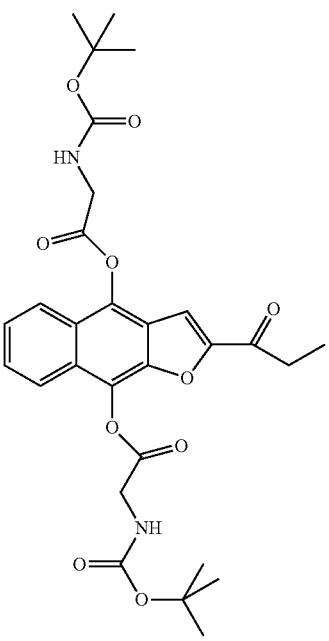
compound VI
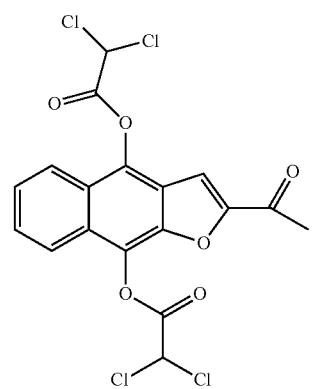
compound VII
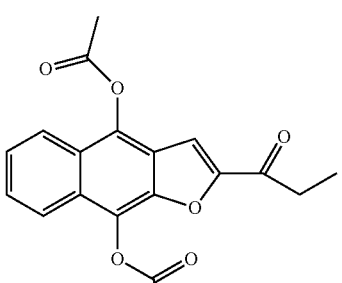
compound VIII
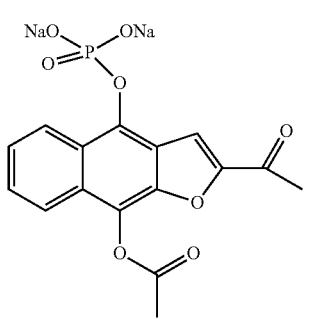

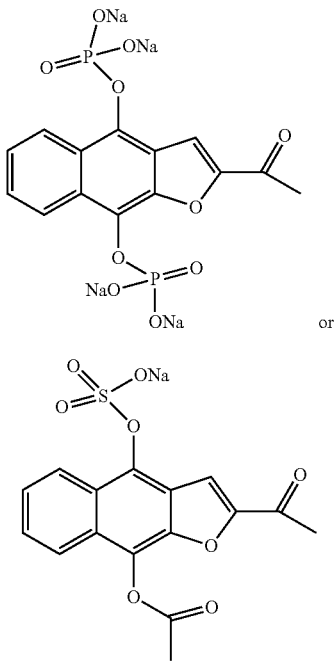

compound IX or compound X

18. A pharmaceutical composition comprising a compound of claim 1, or a pharmaceutically acceptable salt thereof, and a pharmaceutically acceptable excipient, carrier, or diluent.

19. The pharmaceutical composition of claim 18, wherein the compound is an amorphous solid.

20. A method of treating a subject suffering from or susceptible to a disease, disorder, or condition, the method comprising administering to the subject a therapeutically effective amount of a compound of claim 1.

21. The method of claim 20, wherein the disease, disorder, or condition is a proliferative disease, disorder, or condition.

22. The method of claim 20, wherein the disease, disorder, or condition is selected from obesity, an obesity-related disorder or condition, diabetes, metabolic disease, or degenerative disease.

23. The method of claim 21, wherein the disease, disorder, or condition is associated with mitochondrial dysfunction.

24. The method of claim 21, wherein the proliferative disease is cancer.

25. The method of claim 21, further comprising administering to the subject a therapeutically effective amount of a second chemotherapeutic agent.

26. The method of claim 24, wherein the subject is in clinical remission or, where the subject has been treated by surgery, has limited unresected disease.

27. The method of claim 24, wherein the cancer is a solid tumor.

28. The method of claim 27, further comprising treatment of the cancer with radiation therapy.

29. The method of claim 24, wherein the cancer is selected from the group consisting of colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, nasopharyngeal cancer, gallbladder cancer, laryngeal cancer, oral cancer, penile cancer, glandular tumors, rectal cancer, small intestine cancer, head and neck cancer, multiple myeloma, colorectal carcinoma, kaposi sarcoma, ewing's sarcoma, osteosarcoma, leiomyosarcoma, glioma, meningioma, medulloblastoma, melanoma, urethral cancer, and vaginal cancer.

30. The method of claim 29, wherein the cancer is metastatic.

31. The method of claim 29, wherein the subject is a mammal.

* * * * *